United States Patent
Bedford et al.

(10) Patent No.: US 7,553,296 B2
(45) Date of Patent: *Jun. 30, 2009

(54) SAFETY DEVICE WITH TRIGGER MECHANISM

(75) Inventors: Anthony Jonathan Bedford, Harston (GB); David Robert Gale, Harston (GB); Robin Craig Cocker, Harston (GB); Adrian Edward Cooper, Harston (GB)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/894,848

(22) Filed: Aug. 22, 2007

(65) Prior Publication Data

US 2008/0051724 A1 Feb. 28, 2008

Related U.S. Application Data

(63) Continuation-in-part of application No. 10/716,771, filed on Nov. 19, 2003, now Pat. No. 7,300,423.

(30) Foreign Application Priority Data

Feb. 14, 2003 (GB) .................................. 0303437.8

(51) Int. Cl.
*A61M 5/00* (2006.01)
(52) U.S. Cl. .................. 604/162; 604/192; 604/263
(58) Field of Classification Search .................. 604/110, 604/263, 158, 162, 192, 195, 197–199, 164.08, 604/164.07, 177, 165.03, 168.01; 128/919; 600/573, 576

See application file for complete search history.

(56) References Cited

U.S. PATENT DOCUMENTS 1,779,451 A 10/1930 Sponsel (Continued)

FOREIGN PATENT DOCUMENTS

DE 19518803 12/1995

(Continued)

OTHER PUBLICATIONS

International Search Report from European Application No. Ep 08162012.2 dated Dec. 18, 2008.

(Continued)

*Primary Examiner*—Matthew F Desanto

(57) ABSTRACT

A medical safety device is provided and includes a needle hub having a needle supported thereon; and a safety shield operatively mounted on the needle hub. The safety shield includes a pair of spaced legs and a foot member. Each proximal segment includes a camming surface. The safety shield further includes a trigger supported on the foot member. The trigger includes a camming member and is movable to move the camming member into engagement with the camming surfaces of the proximal segments to effect movement of the legs from a first position in which the distal ends of the distal segments shield a distal end of the needle to a second position in which the distal end of the needle is at least partially exposed. The trigger is removably secured to the foot member.

19 Claims, 23 Drawing Sheets

U.S. PATENT DOCUMENTS

| | | |
|---|---|---|
| 2,559,474 A | 7/1951 | Son |
| 2,700,385 A | 1/1955 | Ortiz |
| 2,836,942 A | 6/1958 | Miskel |
| 2,854,976 A | 10/1958 | Heydrich |
| 2,925,083 A | 2/1960 | Craig |
| 2,953,243 A | 9/1960 | Roehr |
| 3,021,942 A | 2/1962 | Hamilton |
| 3,073,307 A | 1/1963 | Stevens |
| 3,074,542 A | 1/1963 | Myerson et al. |
| 3,134,380 A | 5/1964 | Armao |
| 3,255,873 A | 6/1966 | Speelman |
| 3,294,231 A | 12/1966 | Vanderbeck |
| 3,323,523 A | 6/1967 | Scislowicz et al. |
| 3,329,146 A | 7/1967 | Waldman, Jr. |
| 3,333,682 A | 8/1967 | Burke |
| 3,367,488 A | 2/1968 | Hamilton |
| 3,485,239 A | 12/1969 | Vanderbeck |
| 3,537,452 A | 11/1970 | Wilks |
| 3,587,575 A | 6/1971 | Lichtenstein |
| 3,610,240 A | 10/1971 | Harautuneian |
| 3,645,835 A | 2/1972 | Hodgson |
| 3,658,061 A | 4/1972 | Hall |
| 3,828,775 A | 8/1974 | Armel |
| 3,840,008 A | 10/1974 | Noiles |
| 3,890,971 A | 6/1975 | Leeson et al. |
| 3,904,033 A | 9/1975 | Haerr |
| 3,918,446 A | 11/1975 | Buttaravoli |
| 3,934,722 A | 1/1976 | Goldberg |
| 3,968,876 A | 7/1976 | Brookfield |
| 4,040,419 A | 8/1977 | Goldman |
| 4,106,621 A | 8/1978 | Sorenson |
| 4,113,090 A | 9/1978 | Carstens |
| 4,139,009 A | 2/1979 | Alvarez |
| 4,175,008 A | 11/1979 | White |
| 4,270,536 A | 6/1981 | Lemelson |
| 4,300,678 A | 11/1981 | Gyure et al. |
| 4,375,849 A | 3/1983 | Hanifl |
| 4,430,082 A | 2/1984 | Schwabacher |
| 4,592,744 A | 6/1986 | Jagger et al. |
| 4,634,428 A | 1/1987 | Cuu |
| 4,643,722 A | 2/1987 | Smith, Jr. |
| 4,659,330 A | 4/1987 | Nelson et al. |
| 4,664,259 A | 5/1987 | Landis |
| 4,664,654 A | 5/1987 | Strauss |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,725,267 A | 2/1988 | Vaillancourt |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Choksi |
| 4,738,663 A | 4/1988 | Bogan |
| 4,743,233 A | 5/1988 | Schneider |
| 4,747,836 A | 5/1988 | Luther |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,790,828 A | 12/1988 | Dombrowski et al. |
| 4,795,432 A | 1/1989 | Karczmer |
| 4,795,443 A | 1/1989 | Permenter et al. |
| 4,801,295 A | 1/1989 | Spencer |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byrne et al. |
| 4,826,491 A | 5/1989 | Schramm |
| 4,838,871 A | 6/1989 | Luther |
| 4,840,619 A | 6/1989 | Hughes |
| 4,842,587 A | 6/1989 | Poncy |
| 4,846,796 A | 7/1989 | Carrell et al. |
| 4,846,811 A | 7/1989 | Vanderhoof |
| 4,850,968 A | 7/1989 | Romano |
| 4,850,976 A | 7/1989 | Heinrich et al. |
| 4,850,977 A | 7/1989 | Bayless |
| 4,850,978 A | 7/1989 | Dudar et al. |
| 4,850,994 A | 7/1989 | Zerbst et al. |
| 4,850,996 A | 7/1989 | Cree |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,867,172 A | 9/1989 | Haber et al. |
| 4,867,746 A | 9/1989 | Dufresne |
| 4,872,552 A | 10/1989 | Unger |
| 4,874,382 A | 10/1989 | Lindemann et al. |
| 4,874,383 A | 10/1989 | McNaughton |
| 4,874,384 A | 10/1989 | Nunez |
| 4,883,469 A | 11/1989 | Glazier |
| 4,886,503 A | 12/1989 | Miller |
| 4,887,998 A | 12/1989 | Martin et al. |
| 4,888,001 A | 12/1989 | Schoenberg |
| 4,892,107 A | 1/1990 | Haber |
| 4,892,521 A | 1/1990 | Laico et al. |
| 4,898,589 A | 2/1990 | Dolgin et al. |
| 4,900,309 A | 2/1990 | Netherton et al. |
| 4,904,244 A | 2/1990 | Harsh et al. |
| 4,911,694 A | 3/1990 | Dolan |
| 4,911,706 A | 3/1990 | Levitt |
| 4,921,490 A | 5/1990 | Spier et al. |
| 4,927,018 A | 5/1990 | Yang et al. |
| 4,929,241 A | 5/1990 | Kulli |
| 4,935,012 A | 6/1990 | Magre et al. |
| 4,935,013 A | 6/1990 | Haber et al. |
| 4,936,830 A | 6/1990 | Verlier |
| 4,944,397 A | 7/1990 | Miller |
| 4,944,731 A | 7/1990 | Cole |
| 4,950,249 A | 8/1990 | Jagger et al. |
| 4,950,250 A | 8/1990 | Haber et al. |
| 4,978,344 A | 12/1990 | Dombrowski et al. |
| 4,982,842 A | 1/1991 | Hollister |
| 4,985,021 A | 1/1991 | Straw et al. |
| 4,994,041 A | 2/1991 | Dombrowski et al. |
| 4,998,922 A | 3/1991 | Kuracina et al. |
| 5,000,744 A | 3/1991 | Hoffman et al. |
| 5,011,479 A | 4/1991 | Le et al. |
| 5,015,240 A | 5/1991 | Soproni et al. |
| 5,015,242 A | 5/1991 | Heifetz |
| 5,057,089 A | 10/1991 | Greco |
| 5,059,180 A | 10/1991 | McLees |
| 5,059,184 A | 10/1991 | Dyke |
| 5,069,669 A | 12/1991 | Kole |
| 5,092,851 A | 3/1992 | Ragner |
| 5,108,379 A | 4/1992 | Dolgin et al. |
| RE34,045 E | 8/1992 | McFarland |
| 5,135,509 A | 8/1992 | Olliffe |
| 5,139,489 A | 8/1992 | Hollister |
| 5,147,303 A | 9/1992 | Martin |
| 5,154,285 A | 10/1992 | Hollister |
| 5,176,655 A | 1/1993 | McCormick et al. |
| 5,176,656 A | 1/1993 | Bayless |
| 5,193,552 A | 3/1993 | Columbus et al. |
| 5,195,983 A | 3/1993 | Boese |
| 5,209,739 A | 5/1993 | Talalay |
| 5,232,454 A | 8/1993 | Hollister |
| 5,232,455 A | 8/1993 | Hollister |

| | | |
|---|---|---|
| 5,242,417 A | 9/1993 | Paudler |
| 5,242,418 A | 9/1993 | Weinstein |
| 5,246,427 A | 9/1993 | Sturman et al. |
| 5,246,428 A | 9/1993 | Falknor |
| 5,250,031 A | 10/1993 | Kaplan et al. |
| 5,254,099 A | 10/1993 | Kuracina et al. |
| 5,256,152 A | 10/1993 | Marks |
| 5,256,153 A | 10/1993 | Hake |
| 5,277,311 A | 1/1994 | Hollister |
| 5,290,255 A | 3/1994 | Vallelunga et al. |
| 5,295,963 A | 3/1994 | Deeks |
| 5,295,972 A | 3/1994 | Mischenko |
| 5,304,137 A | 4/1994 | Fluke |
| 5,312,368 A | 5/1994 | Haynes |
| 5,312,369 A | 5/1994 | Arcusin et al. |
| 5,334,158 A | 8/1994 | McLees |
| 5,348,544 A | 9/1994 | Sweeney et al. |
| 5,356,387 A | 10/1994 | Sirbola |
| 5,356,392 A | 10/1994 | Firth et al. |
| 5,372,589 A | 12/1994 | Davis |
| 5,374,255 A | 12/1994 | Nathan et al. |
| 5,403,283 A | 4/1995 | Luther |
| 5,403,286 A | 4/1995 | Lockwood, Jr. |
| 5,407,436 A | 4/1995 | Toft et al. |
| 5,411,492 A | 5/1995 | Sturman et al. |
| 5,423,765 A | 6/1995 | Hollister |
| 5,423,766 A | 6/1995 | Di Cesare |
| 5,425,720 A | 6/1995 | Rogalsky et al. |
| 5,445,618 A | 8/1995 | Adobbati |
| 5,447,501 A | 9/1995 | Karlsson et al. |
| 5,466,223 A | 11/1995 | Bressler et al. |
| 5,480,385 A | 1/1996 | Thorne et al. |
| 5,486,164 A | 1/1996 | Streck |
| 5,487,733 A | 1/1996 | Caizza et al. |
| 5,487,734 A | 1/1996 | Thorne et al. |
| 5,490,841 A | 2/1996 | Landis |
| 5,498,243 A | 3/1996 | Vallelunga et al. |
| 5,531,694 A | 7/1996 | Clemens et al. |
| 5,533,980 A | 7/1996 | Sweeney et al. |
| 5,536,240 A | 7/1996 | Edwards et al. |
| 5,538,508 A | 7/1996 | Steyn |
| 5,542,927 A | 8/1996 | Thorney et al. |
| 5,549,568 A | 8/1996 | Shields |
| 5,549,570 A | 8/1996 | Rogalsky |
| 5,549,708 A | 8/1996 | Thorne et al. |
| 5,562,629 A | 10/1996 | Haughton et al. |
| 5,562,631 A | 10/1996 | Bogert |
| 5,573,510 A | 11/1996 | Isaacson |
| 5,584,816 A | 12/1996 | Gyure et al. |
| 5,584,818 A | 12/1996 | Morrison |
| 5,599,318 A | 2/1997 | Sweeney et al. |
| 5,603,699 A | 2/1997 | Shine |
| 5,611,782 A | 3/1997 | Haedt |
| 5,643,220 A | 7/1997 | Cosme |
| 5,672,161 A | 9/1997 | Allen et al. |
| 5,693,022 A | 12/1997 | Haynes |
| 5,695,474 A | 12/1997 | Daugherty |
| 5,695,477 A | 12/1997 | Sfikas |
| 5,700,249 A | 12/1997 | Jenkins |
| 5,735,827 A | 4/1998 | Adwers et al. |
| 5,738,665 A | 4/1998 | Caizza et al. |
| 5,746,718 A | 5/1998 | Steyn |
| 5,746,726 A | 5/1998 | Sweeney et al. |
| 5,755,699 A | 5/1998 | Blecher et al. |
| 5,814,018 A | 9/1998 | Elson et al. |
| 5,817,064 A | 10/1998 | DeMarco et al. |
| 5,823,997 A | 10/1998 | Thorne |
| 5,843,041 A | 12/1998 | Hake et al. |
| 5,879,330 A | 3/1999 | Bell |
| 5,891,092 A | 4/1999 | Castellano |
| 5,910,130 A | 6/1999 | Caizza et al. |
| 5,910,132 A | 6/1999 | Schultz |
| 5,919,168 A | 7/1999 | Sheeler |
| 5,921,969 A | 7/1999 | Vallelunga et al. |
| 5,925,020 A | 7/1999 | Nestell |
| 5,951,522 A | 9/1999 | Rosato et al. |
| 5,951,525 A | 9/1999 | Thorne et al. |
| 5,957,892 A | 9/1999 | Thorne |
| 5,976,111 A | 11/1999 | Hart |
| 5,980,488 A | 11/1999 | Thorne |
| 5,997,504 A | 12/1999 | Bell |
| 6,015,397 A | 1/2000 | Elson et al. |
| 6,036,675 A | 3/2000 | Thorne et al. |
| 6,149,629 A | 11/2000 | Wilson et al. |
| 6,171,284 B1 | 1/2001 | Kao et al. |
| RE37,110 E | 3/2001 | Hollister |
| 6,224,576 B1 | 5/2001 | Thorne et al. |
| RE37,252 E | 7/2001 | Hollister |
| 6,254,575 B1 | 7/2001 | Thorne, Jr. et al. |
| 6,280,420 B1 | 8/2001 | Ferguson et al. |
| 6,334,857 B1 | 1/2002 | Hollister et al. |
| 6,582,397 B2 | 6/2003 | Alesi et al. |
| 6,592,556 B1 | 7/2003 | Thorne |
| 6,635,032 B2 | 10/2003 | Ward, Jr. |
| 6,719,731 B2 | 4/2004 | Parmigiani |
| 7,300,423 B2 * | 11/2007 | Cocker et al. ............... 604/263 |
| 2001/0039401 A1 | 11/2001 | Ferguson et al. |
| 2002/0004650 A1 | 1/2002 | Kuracina et al. |
| 2002/0072716 A1 | 6/2002 | Barrus et al. |
| 2002/0193748 A1 | 12/2002 | Cocker et al. |
| 2003/0004465 A1 | 1/2003 | Ferguson et al. |
| 2003/0181870 A1 | 9/2003 | Bressler et al. |
| 2003/0181871 A1 | 9/2003 | Wilkinson et al. |

FOREIGN PATENT DOCUMENTS

| | | |
|---|---|---|
| EP | 0 144 483 | 6/1985 |
| EP | 0 815 890 A2 | 1/1988 |
| EP | 0 344 606 A2 | 12/1989 |
| EP | 0 457 477 B1 | 11/1991 |
| EP | 0 485 345 B1 | 5/1992 |
| EP | 0 533 308 A1 | 3/1994 |
| EP | 0 585 391 B1 | 3/1994 |
| EP | 0 597 857 B1 | 5/1994 |
| EP | 0 603 365 B1 | 6/1994 |
| EP | 0 626 924 B1 | 12/1994 |
| EP | 0 654 281 B1 | 5/1995 |
| EP | 0 705 613 B1 | 4/1996 |
| EP | 0 713 710 A1 | 5/1996 |
| EP | 1 807 443 A2 | 11/1997 |
| EP | 0 815 888 A2 | 1/1998 |
| EP | 0 819 441 A1 | 1/1998 |
| EP | 0 832 659 A2 | 4/1998 |
| EP | 0 832 660 A2 | 4/1998 |
| EP | 1 092 443 A2 | 4/2001 |
| EP | 1 116 493 A1 | 7/2001 |
| GB | 1233302 | 5/1971 |
| GB | NL9000909 | 4/1990 |
| GB | NL9001664 | 7/1990 |
| GB | NL 9001664 * | 7/1990 |
| GB | 2283429 A | 5/1995 |
| GB | 2 301 036 | 11/1996 |
| GB | 2369779 | 12/2002 |
| JP | 10-76007 | 3/1998 |
| JP | 10-127765 | 5/1998 |
| WO | WO 87/07162 | 12/1987 |
| WO | WO 89/04681 | 6/1989 |
| WO | WO 89/07955 | 9/1989 |
| WO | WO 93/02728 | 2/1993 |
| WO | WO 93/17732 | 9/1993 |
| WO | WO 94/01152 | 1/1994 |
| WO | WO 94/19036 | 9/1994 |
| WO | WO 97/31666 | 4/1997 |
| WO | WO 98/07463 | 2/1998 |
| WO | WO 98/10816 | 3/1998 |
| WO | WO 98/11928 | 3/1998 |

| | | |
|---|---|---|
| WO | WO 98/13081 | 4/1998 |
| WO | WO 00/16832 | 3/2000 |
| WO | WO 00/38765 | 6/2000 |
| WO | WO 01/32241 A1 | 5/2001 |
| WO | WO 01/32244 A1 | 5/2001 |
| WO | WO 2004/071559 A1 | 8/2004 |

OTHER PUBLICATIONS

International Search Report from Indian Application No. 2473/DELNP/2005 dated Nov. 2, 2007.

* cited by examiner

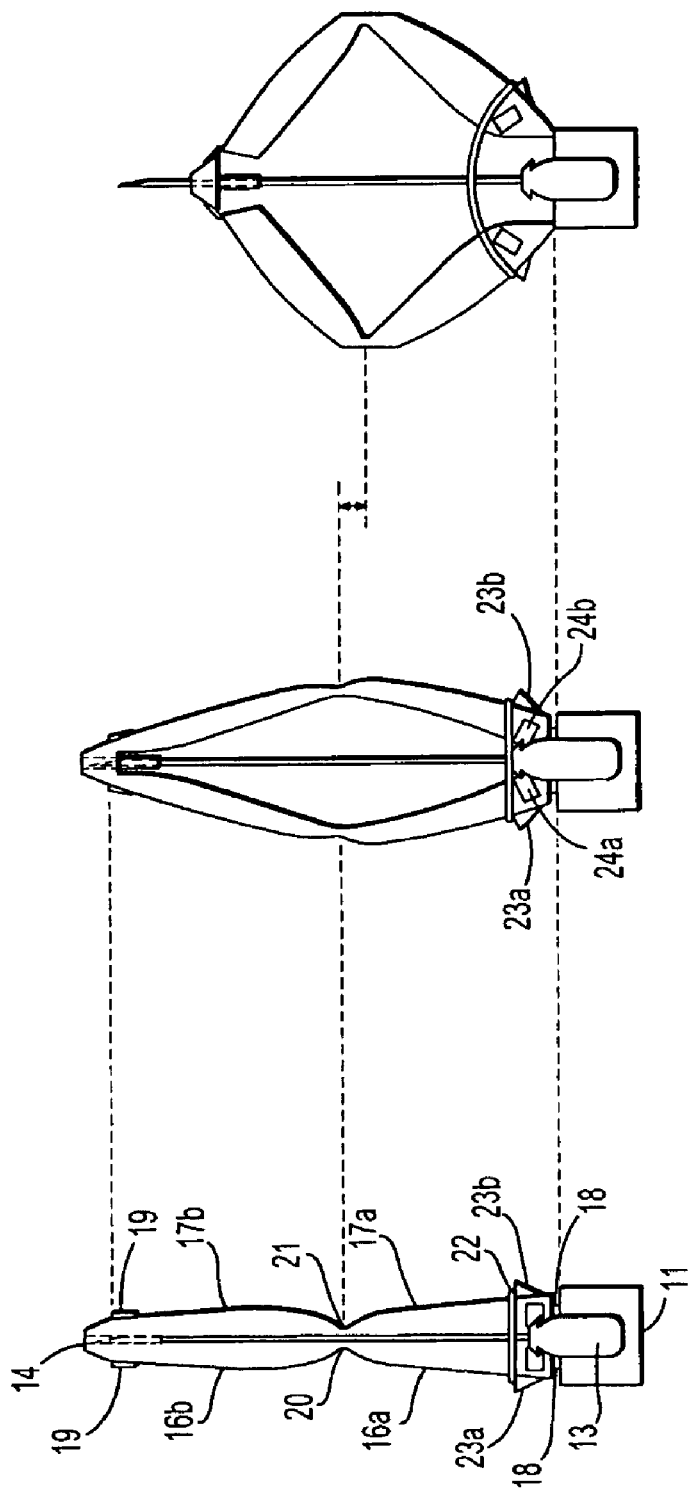
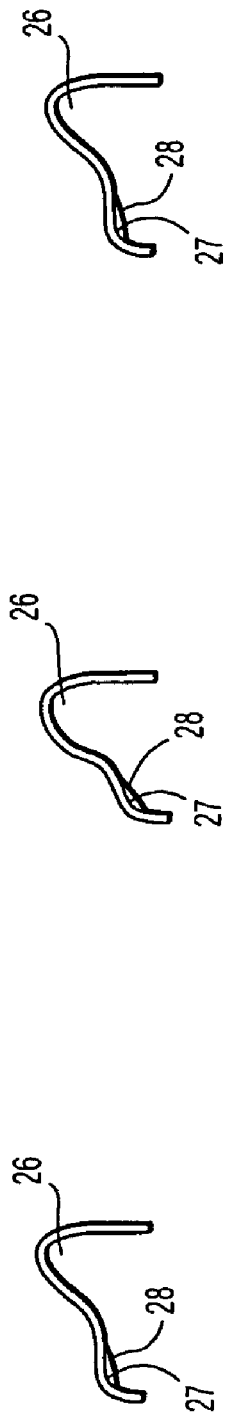
FIG. 3A  FIG. 3B  FIG. 3C

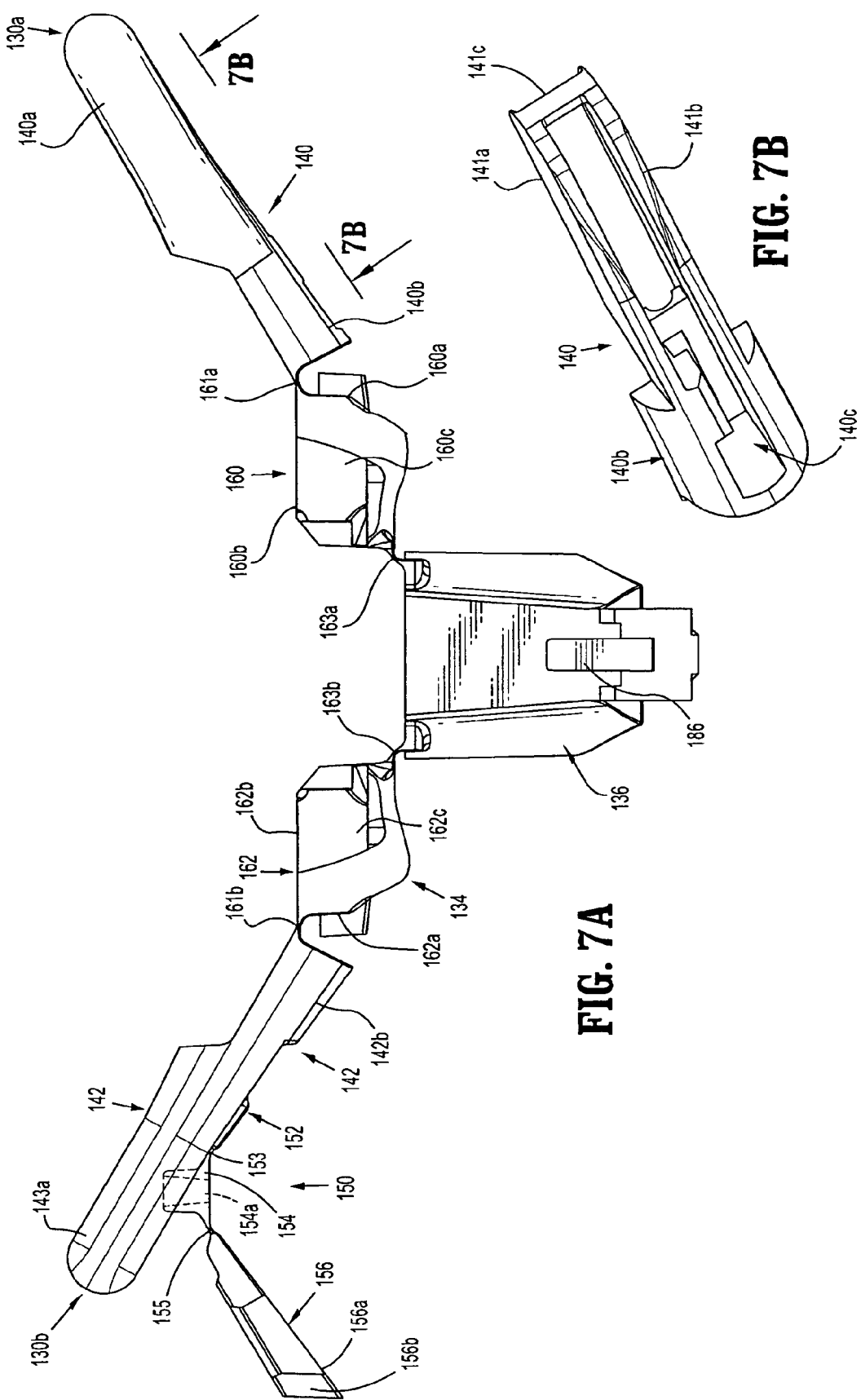

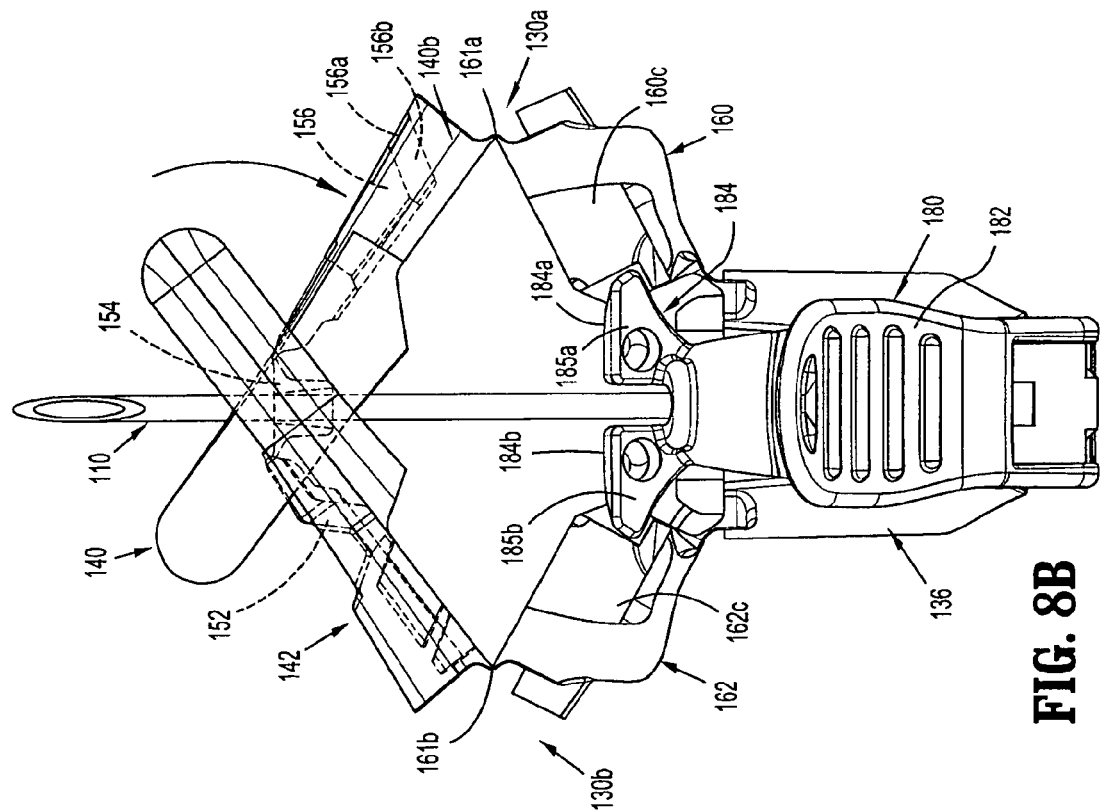
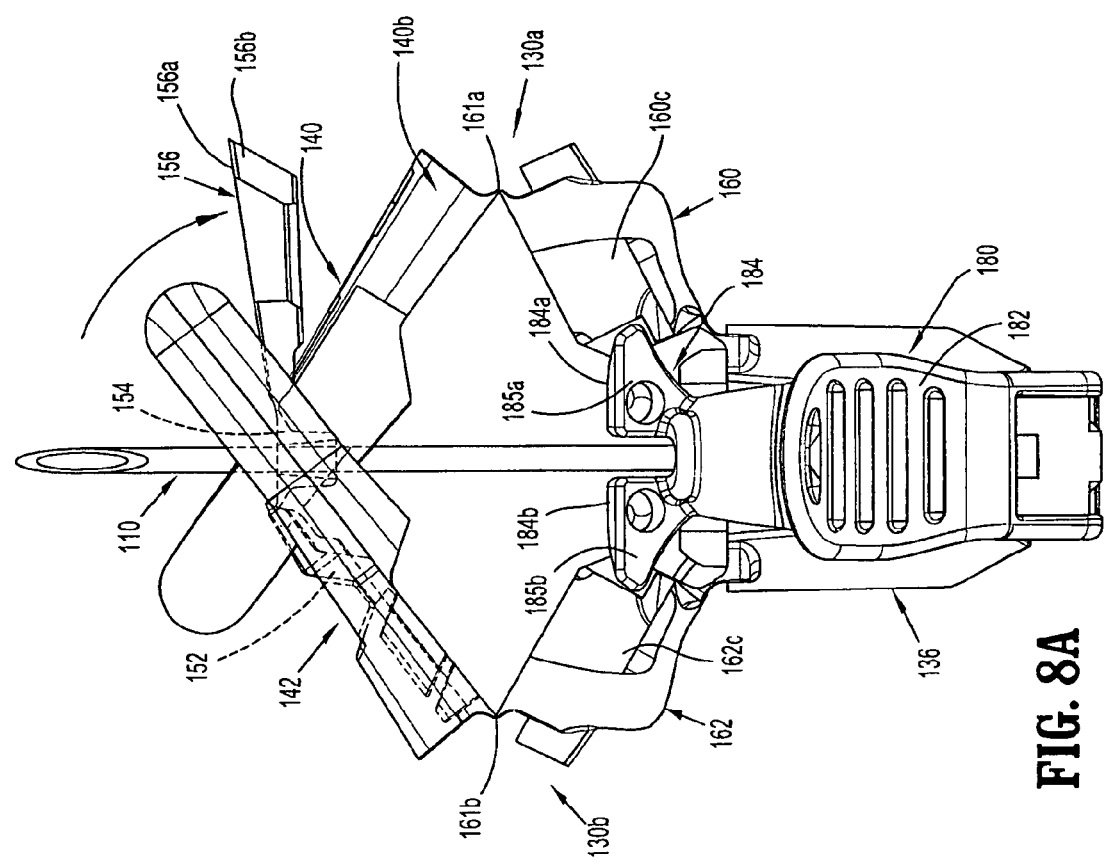
FIG. 8A
FIG. 8B

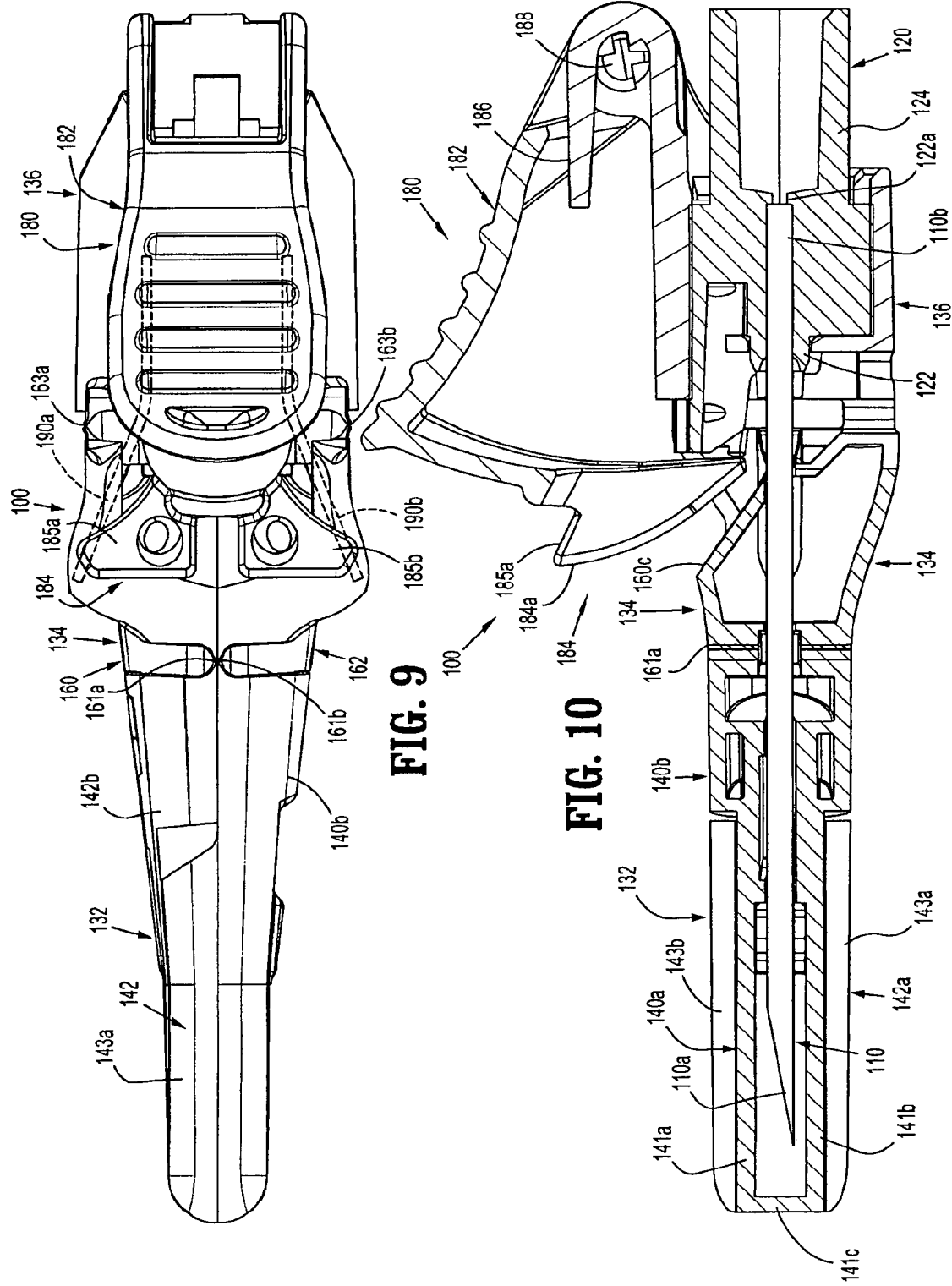

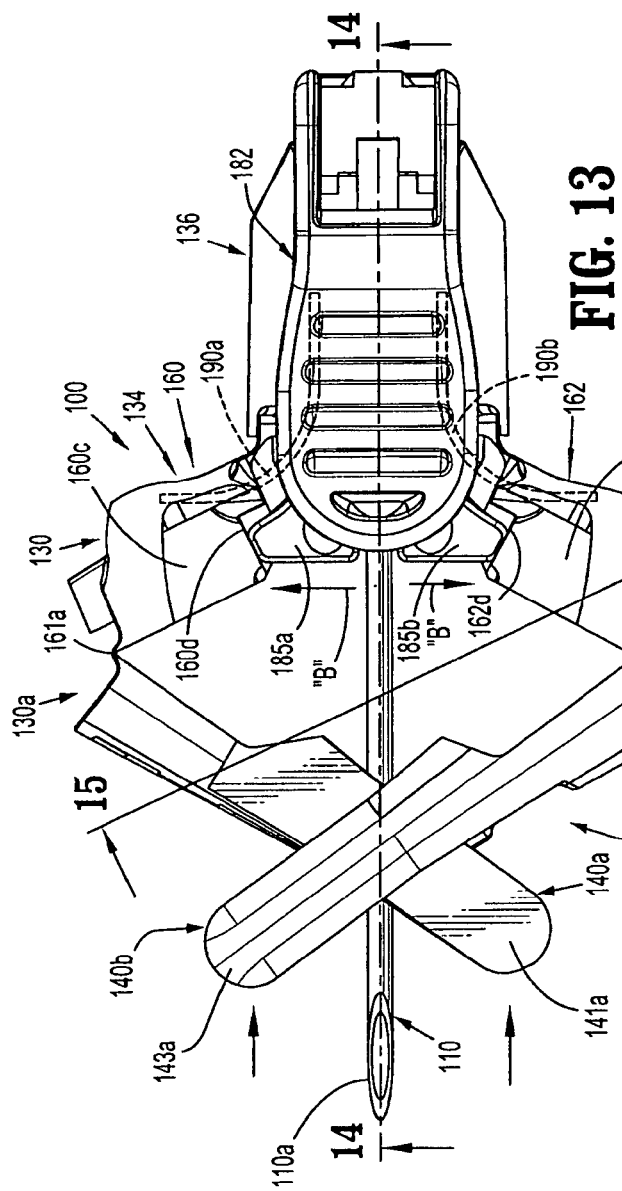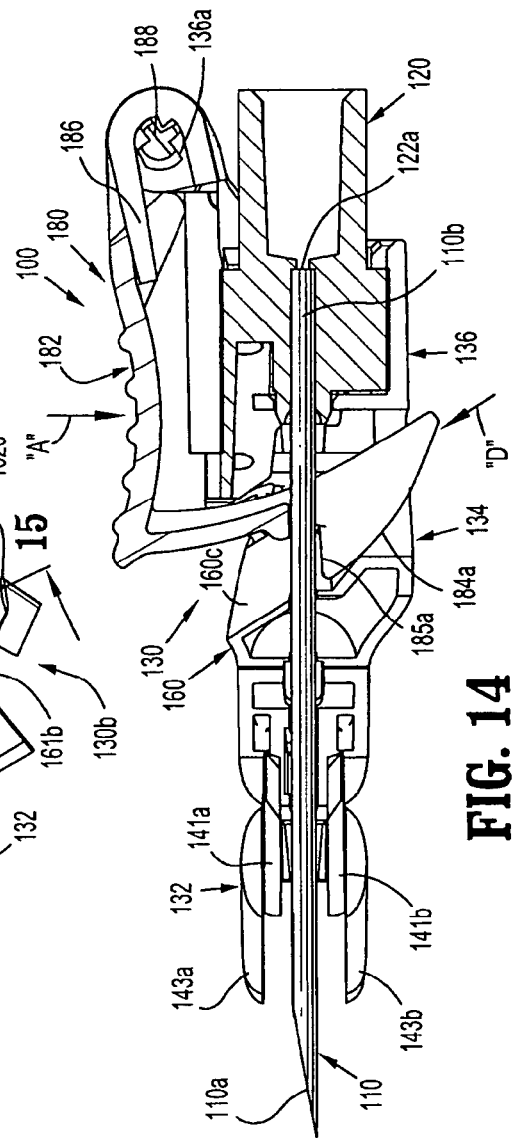

SAFETY DEVICE WITH TRIGGER MECHANISM

CROSS-REFERENCE TO RELATED APPLICATIONS

The present application is a Continuation-in-Part application which claims the benefit of and priority to U.S. application Ser. No. 10/716,771, filed on Nov. 19, 2003 now U.S. Pat. No. 7,300,423, which in turn claims the benefit of and priority to GB Application Serial No. 0303437.8, filed on Feb. 14, 2003, the entire content of each of which being incorporated herein by reference.

BACKGROUND

1. Technical Field

The present invention relates to safety devices and a method of manufacture thereof and, more particularly, to medical devices including hypodermic needles having a safety device provided therewith and methods of manufacturing the same.

2. Background of Related Art

There is a known problem associated with hypodermic needles, which is that once a hypodermic needle has been used on a patient, it may be contaminated with an infection from the patient, and there is therefore a risk that the needle may pass on the infection if it is allowed to come into contact with another person. Similarly, if a needle accidentally pricks one person before it is used on a patient, an infection may be passed onto the patient from the person accidentally pricked. Undesirable pricking of this nature will hereinafter be referred to as "needle stick".

A number of safety devices have been proposed in an attempt to counter the above described problems. Some such devices are combined needle and syringe arrangements in which the needle may be retracted into the body of the syringe by applying additional pressure on the syringe plunger once it has been pushed to the end of the syringe cylinder (i.e. once all of the fluid to be injected has been ejected from the syringe). While the syringe and needle arrangement is transported and stored, a plastic cap is fitted over the needle. There are a number of problems with a device of this type. Firstly, this device is only suitable for injecting fluid into a patient and not for taking a sample from a patient because the retraction of the needle is activated once the plunger is fully pushed into the cylinder and not when it is partially withdrawn from the cylinder as would be the case after the taking of a sample. Also, the person who is to give the injection must remove the plastic cap some time before the injection takes place, and from this moment on until the needle is retracted, the device is unsafe. Once the injection is completed, the operator of the needle must remember to perform the action to cause the needle to retract. To maximize safety, this should be performed whilst the needle is still within the patient. However, this is painful for the patient. Also, the operator may simply omit to retract the needle for whatever reason, thus leaving the needle exposed and unsafe.

To counter this last problem, it has been proposed to include a time fuse mechanism which is activated upon, for example, hydration (e.g. by receiving a blood sample or a liquid to be injected into the syringe). However, the needle will be unsafe for the duration of the time fuse period and can cause problems if, for example, the retraction is automatically activated during an injection.

U.S. Pat. No. 5,976,111 describes an alternative safety device for a hypodermic needle. The described device includes a stem portion through which fluid may flow between the syringe mounted on a proximal end of the stem and a needle mounted on a distal end of the stem. Telescopically mounted around the stem is a sheath cylinder. The sheath cylinder may slide over the stem from a first, exposed, position in which the point of the needle is exposed, to a second position in which the whole of the needle is covered by the sheath. A helical metal spring urges the sheath into the second position. A pair of leaf spring arms which are biased radially outwardly are mounted onto the stem and lock the sheath in the second position (the needle is therefore safe while the sheath is locked in the second position). A ring is also slidably mounted on the stem and may be used to unlock the sheath by forcing the leaf spring arms flat into the stem portion to permit an injection to take place. During an injection the skin of the patient pushes the sheath cylinder (and also the unlocking ring) back into the first position, exposing the needle point which may therefore pierce the patient's skin. Upon completion of the injection, the sheath is urged back (due to the spring) into the second position as the needle is withdrawn from the patient, thus re-covering the needle. While the sheath is pushed back over the stem portion towards the first position, the unlocking ring is also pushed back into a position where it no longer restrains the leaf spring arms; therefore, when the sheath cylinder returns back to the second "safe" position the leaf spring arms are released and they spring out into locking engagement with the sheath to prevent the sheath from sliding back into the first, exposed, position again.

The device described in U.S. Pat. No. 5,976,111 satisfies many of the safety requirements associated with hypodermic needles discussed above. However, it nonetheless suffers from a number of problems, which it would be desirable to overcome. All of the described embodiments of the device require at least five separate components to be manufactured and then assembled. This renders the cost of the device significantly more than a conventional needle and needle-luer combination (a needle-luer is a small member which is adapted to fit onto a syringe and into which the base of the needle is mounted). Also, because the needle is mounted directly to the stem of the described safety device, a needle manufacturer would have to significantly alter its conventional manufacturing process for producing needle and needle-luer combinations to manufacture the described device.

The present invention seeks to provide an alternative safety device for a hypodermic needles and the like.

SUMMARY

According to an aspect of the present disclosure, a medical safety device is provided. The medical safety device includes a needle hub having a needle supported thereon; and a safety shield operatively mounted on the needle hub. The safety shield includes a pair of spaced legs and a foot member. Each of the legs has a distal segment and a proximal segment, each of the proximal segments has a proximal end hingedly attached to the foot member and a distal end hingedly attached to the distal segment at a hinge member, and each proximal segment includes a camming surface. The safety shield further includes a trigger supported on the foot member. The trigger includes a camming member and is movable to move the camming member into engagement with the camming surfaces of the proximal segments to effect movement of the legs from a first position in which the distal ends of the distal segments shield a distal end of the needle to a second position in which the distal end of the needle is at least partially exposed. The trigger is removably secured to the foot member such that, in use, the trigger can be removed from the foot member to prevent movement of the legs from the first position to the second position.

In an embodiment, when the medical safety device is in the first position, the distal and proximal segments are substantially linearly aligned with the hinge member of each leg positioned adjacent the needle such that when a force is applied to the distal end of the distal segments, the legs are retained in the first position.

The camming member of the trigger and the camming surfaces of the proximal segments may be positioned and configured such that movement of the camming member of the trigger into engagement with the camming surfaces of the proximal segments splays the hinge member of each of the legs outwardly to retract the distal end of each of the distal segment proximally towards the foot member.

Each of the legs may define a channel dimensioned to receive the needle.

The trigger may be pivotally secured to the foot member. The trigger may include an attachment end configured for selective pivotable attachment to the foot member. The attachment end of the trigger may include a pair of ears each including a pin extending therefrom for pivotable engagement in a complementary feature formed in the foot member.

The medical safety device may further include a biasing member configured to urge the legs to the first position. The biasing member may include a piece of spring wire engaging each leg. Each piece of spring wire may have a first end secured to the foot member and a second end extending along at least a portion of a respective leg.

The camming member of the trigger may include a pair of spaced cam portions. Each of the cam portions may be configured to engage one of the camming surfaces of the proximal segments. Each of the camming portions may include a substantially tapered profile having a narrow distal end and an enlarged proximal end.

The proximal end of each camming portion may define an engaging surface for engaging a shoulder on one of the proximal segments. The distal end of at least one of the camming portions may extend below a bottom-most surface of the safety shield.

The medical device may further include an interengaging element positioned between and interconnecting the distal segments of the legs. The interengaging element may include a needle guide defining a lumen dimensioned to slidably receive the needle.

The medical safety device may further include a biasing member positioned to urge the trigger out of engagement with the camming surfaces of the proximal segments.

The camming member of the trigger may include at least one engaging surface and the camming surfaces of the proximal segments may include at least one shoulder. The at least one engaging surface may be movable into engagement with the at least one shoulder to retain the trigger in engagement with the proximal segments and retain the legs in the second position.

According to a further aspect of the present disclosure, a medical safety device is provided. The medical safety device includes a safety shield adapted to be operatively mounted on a needle hub. The safety shield includes a pair of spaced legs and a foot member. Each of the legs has a distal segment and a proximal segment, each of the proximal segments has a proximal end hingedly attached to the foot member and a distal end hingedly attached to the distal segment at a hinge member, and each proximal segment includes a camming surface. The safety shield further includes a trigger supported on the foot member. The trigger includes a camming member and is movable to move the camming member into engagement with the camming surfaces of the proximal segments to effect movement of the legs from a first position in which the distal ends of the distal segments shield a distal end of the needle to a second position in which the distal end of the needle is at least partially exposed. The safety shield further includes a piece of spring wire secured to each leg. The piece of spring wire has a proximal end engaging the foot member and a distal end extending along at least a portion of a respective one of the legs. The pieces of spring wire urges the legs to the first position.

According to still another embodiment of the present disclosure, a medical safety device is provided and includes a needle hub having a needle supported thereon; and a safety shield operatively mounted on the needle hub. The safety shield includes a pair of spaced legs and a foot member. Each of the legs has a distal segment and a proximal segment, each of the proximal segments has a proximal end hingedly attached to the foot member and a distal end hingedly attached to the distal segment at a hinge member, and each proximal segment includes a camming surface. The safety shield further includes a trigger supported on the foot member. The trigger includes a camming member and is movable to move the camming member into engagement with the camming surfaces of the proximal segments to effect movement of the legs from a first position in which the distal ends of the distal segments shield a distal end of the needle to a second position in which the distal end of the needle is at least partially exposed. The camming member is configured to extend below a bottom surface of the foot member when pressed into engagement with the camming surfaces of the proximal segments.

The camming member may include a pair of spaced cam portions which define a channel dimensioned to receive the needle. Each of the cam portions may include a substantially tapered profile having a narrow distal end and an enlarged proximal end.

The distal end of the first leg may be confined within the second leg when the legs are in the first position. The distal end of the second leg may be rounded and tapered.

BRIEF DESCRIPTION OF THE DRAWINGS

The accompanying drawings show, by way of example only, safety device trigger mechanisms embodying the invention.

FIGS. 3a, 3b and 3c are schematic cross-sectional views illustrating the effect of the trigger mechanism on the geometry of the safety device in respectively the unprimed, primed and the automatic release from primed positions;

FIG. 7A is a top, plan view of the safety device in an un-assembled condition, with a trigger removed therefrom;

FIG. 7B is a cross-sectional view of a distal portion of the safety device, as taken through 7B-7B of FIG. 7A;

FIG. 8A is a top, plan view of the safety device of FIGS. 5-7D, illustrating an exemplary first step in the assembly thereof;

FIG. 8B is a top, plan view of the safety device of FIGS. 5-7D, illustrating an exemplary second step in the assembly thereof;

FIG. 9 is a top, plan view of the safety device of FIG. 5-8B;

FIG. 10 is a longitudinal, cross-sectional view of the safety device of FIGS. 5-9, as taken through 10-10 of FIG. 5;

FIG. 13 is a top, plan view of the safety device of FIGS. 5-12, illustrating the safety device being actuated to the primed condition;

FIG. 14 is a longitudinal, cross-sectional view of the safety device of FIG. 13, as taken through 14-14 thereof;

DETAILED DESCRIPTION OF EMBODIMENTS

Figure 1:
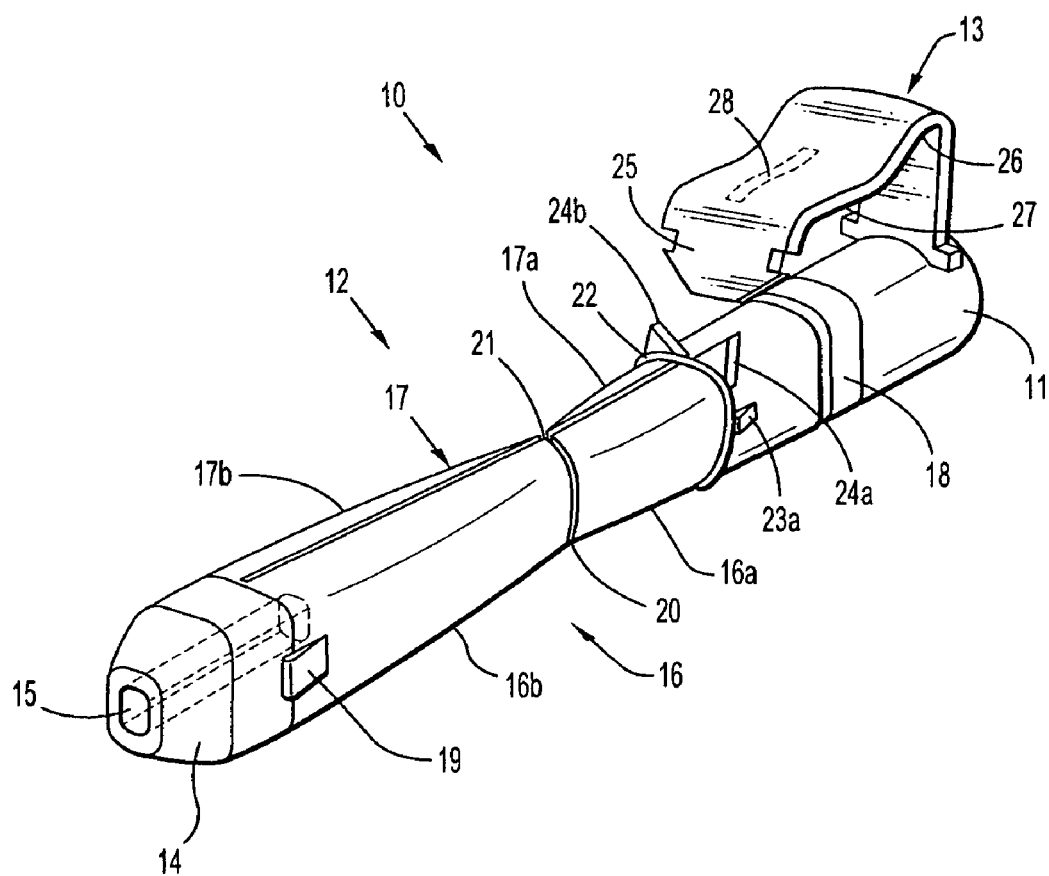
FIG. 1 is a perspective view of the safety device and trigger mechanism according to the invention in which the trigger mechanism is in the unprimed position.
Figure 2:
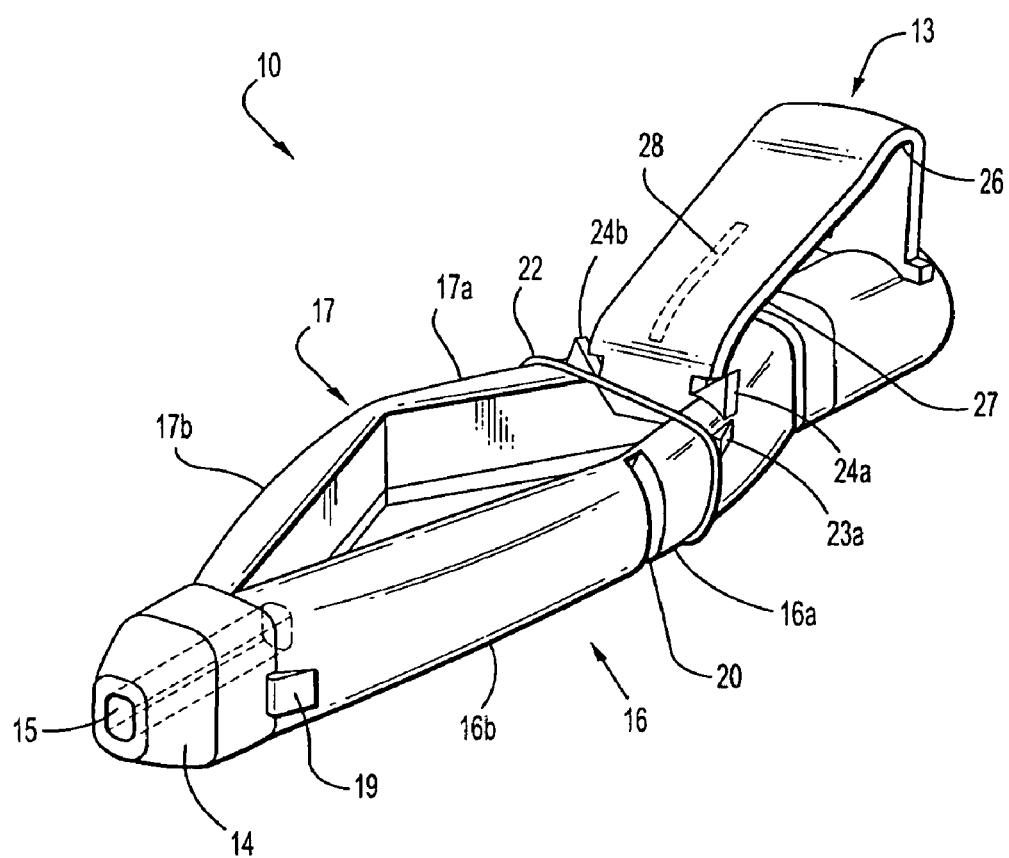
FIG. 2 is a perspective view showing that same trigger mechanism in the primed position.
Figure 4A:
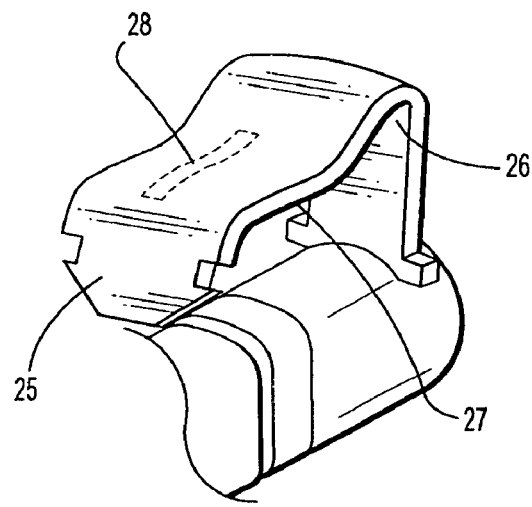
FIG. 4a is an enlarged perspective view of the trigger mechanism.
Figure 4B:
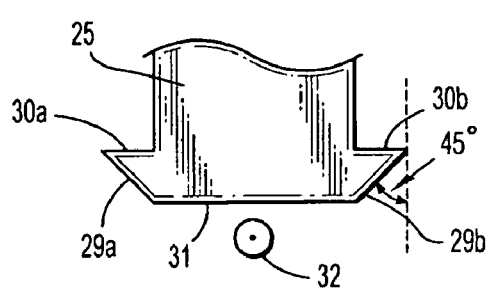
FIG. 4b is a profile of the trigger mechanism.
Figure 4C:
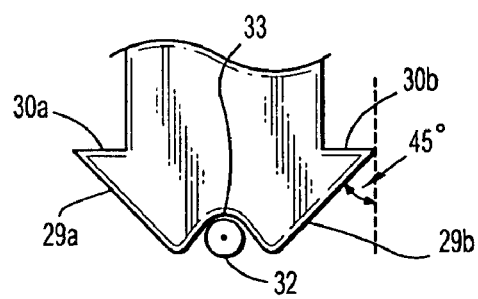
FIG. 4c is a preferred profile of the trigger mechanism.
Figure 4D:
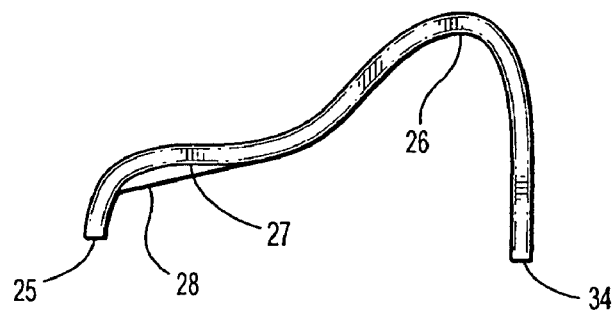
FIG. 4d is a schematic cross-sectional view of the trigger mechanism.

With reference to FIGS. 1 to 4 a safety device assembly 10 is presented comprising a needle receiving portion 11, a sheath portion 12 and a trigger mechanism 13.

The needle-receiving portion 11 operably receives and holds a needle (see FIGS. 3a, 3b, 3c) and/or a needle luer combination and assembly of such.

The sheath portion 12 comprises a nose plate 14 having a bore 15 therethrough, with resiliently flexible legs 16, 17 extending between the needle receiving portion 11 and the nose plate 14 and operably connected at these junctures by hinges 18, 19 on both legs 16, 17.

The safety device assembly 10 is formed by a one piece injection moulding process.

Each resiliently flexible leg 16, 17 of the safety device 10 has a central knee joint 20, 21 separating the back portion of the legs 16a, 17a and the front portion of the legs 16b, 17b. The configuration of the leg portions 16a, 17a; and knee joints 20, 21 ensure that longitudinal forces acting on the nose plate 14 reinforce the natural bias. Resilient means in the form of an elastic band 22 disposed over the rear portion of the legs 16a, 17a prevents deforming and outward flexing of the legs 16, 17 increasing resistance to accidental needle stick when the assembly is unprimed and ensuring automatic return of arms 16, 17 and the nose plate 14 to the extended position when the assembly is no longer in the primed position. The band 22 is held in place by securing lugs 23a, 23b disposed on opposing legs 16a, 17a on the outside face of the legs 16a, 17a. Intermediate the securing lugs 23a, 23b disposed the upper face of the legs 16a, 17a is located release means 24 comprising rigid tabs 24a, 24b. The tabs 24a, 24b form a triangular cut-out region which acts as a lead-in for the trigger mechanism 13.

The trigger mechanism 13 comprises an elongate actuating lever 13 fixably attached at one end to the needle receiving portion 11 and having a second end disposed over the back region of the legs 16, 17 when forced between tabs 24a, 24b it separates the legs 16, 17 in a direction away from each other, overcoming the inherent bias of the legs 16, 17 and the restraining force of band 22.

The tab-engaging portion 25 of the lever 13 is shaped and sized to engage the release means 24 and separate the rigid tabs 24a, 24b when pressed in a downward direction and in turn separate the legs 16, 17 whilst not obstructing the passage of the needle.

The profile of the elongate actuator lever 13 comprises a large radius 26 at the rear and a smaller radius 27 at the front. A strengthening rib 28 on the underside of the actuating lever 13 is disposed between the engaging portion 25 and the entirety of the small radius 27.

In operation, a user would grasp the safety device assembly 10 by placing a thumb on the upper face of the trigger lever 13 above the strengthening rib 28 whilst at the same time having a finger, on the underside of the assembly, supporting the assembly when the user then presses the trigger, the pressure of such a movement forces the engaging portion of the actuating lever 13 between the release means 24 and separates the tabs 24a, 24b, the engaging portion 25 is progressively securely latched between and under each leg 16a, 17a in a position immediately below the tabs 24a, 24b.

In this, the so-called primed position, subsequently applied longitudinal forces acting on the nose plate 14 will cause the legs 16, 17 to flex outwardly and unsheath the needle for use. Performing the injection (i.e. continuing such longitudinal application of force along the needle axis) causes the legs 16, 17 to flex apart to a maximum position and the actuating lever 13 engaging portion 25 is then released from its secured latched position and rises up, under its own resilience, out of the way of the legs.

When the longitudinal force acting on the nose plate 14 is removed, the needle retracts; the natural resilience of the legs 16, 17 plus the action of band 22 causes the legs 16, 17 to automatically close around the needle until they are once more in the closed position of FIG. 1. They are then geometrically so biased that further longitudinal forces acting on the nose plate 14 will be resisted rather than cause the needle to be exposed.

The double-curved profile of the trigger mechanism 13 gives it in-built equilibrium retaining the relative positions between the engaging portion above the release means 24. Its shape also intuitively leads the user to correctly use the assembly 10 to perform an injection. In other words, he will tend naturally to downwardly press it rather than attempt to push it forwards.

The trigger has a number of other advantageous features.

The downward engaging movement of portion 25 as it separates the legs 16, 17 is such that further downward pressure as the engaging portion 25 is latched into a primed position tends to retain inline the centers of the legs 20, 21 and the centre of the needle.

The end profile of the engaging portion 25 is so shaped to separate the arms 16, 17 evenly whilst retaining the geometry of the legs 16, 17—if the centers of the legs 20, 21 are not kept far enough apart one leg would have a tendency to lock and hinder movement but the present configuration ensure both legs 16, 17 move apart equally.

The end profile has a squared off front end, so that when the engaging portion 25 is latched in the primed position there is sufficient clearance for the needle to move without impacting the trigger mechanism 13. In an alternative embodiment (FIG. 4c) it is so shaped and sized to embrace the needle without restricting movement of the needle; this is also advantageous in its own right.

The curvy profile of the actuating lever 13 comprises two radii, a large rearward radius 26 to prevent the likelihood of plastic creep giving the assembly 10 a longer life, inherent-reusability and to assist the spring back action of the lever 13 and a smaller forward radius 27 giving the so-called working end of the lever 13 with the engaging portion 25 a low profile.

The strengthening rib 28 limits the deformation of the curved shape trigger 13, in use. It permits deformation in the first curve 26 which in turn assists spring-back but strengthens the second curve 27 restricting the movement of the engaging portion 25 downwards rather than forwards.

Turning now to FIGS. 5-21, a medical safety device according to another embodiment of the present disclosure, is generally shown as 100.

Medical safety device 100 includes a syringe needle 110 supported on a needle hub 120, and a safety shield 130 operatively mounted on needle hub 120 and operatively associated with syringe needle 110. A distal end 110a of syringe needle 110 is tapered to enable tissue penetration and the like, a proximal end 110b of syringe needle 110 is fluidly connected to or supported within needle hub 120.

Figure 6:
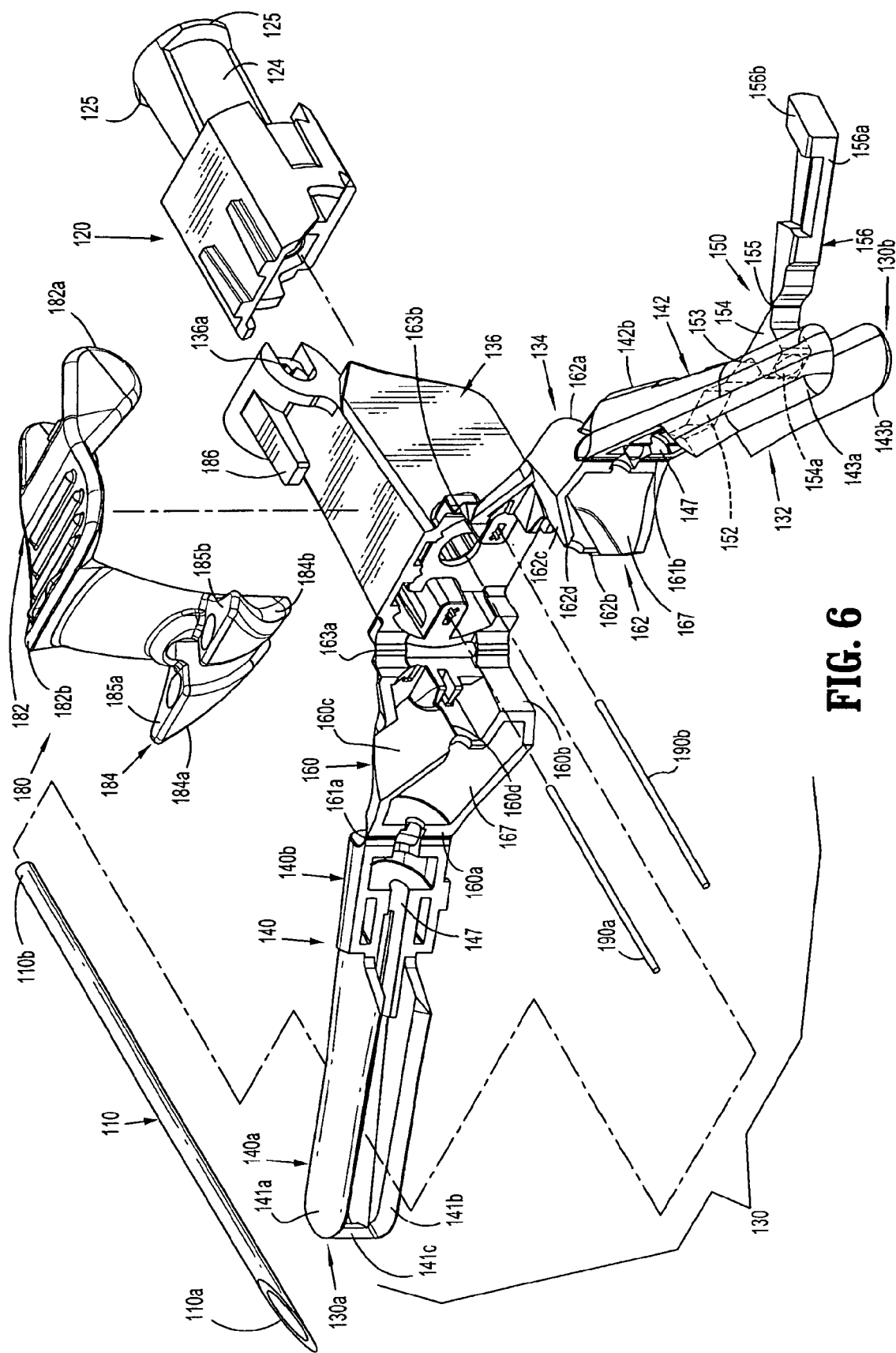
FIG. 6 is an exploded, perspective view of the safety device of FIG. 5.

As seen in FIG. 6, needle hub 120 includes a Luer-type connector having a needle support 122 defining a lumen 122a (see FIG. 10) therethrough for support of syringe needle 110 therein, and a hub skirt 124 spaced radially apart from and extending around needle support 122. Hub skirt 124 defines a pair of radially opposed flanges 125 extending therefrom for engagement with threads (not shown) formed in a collar of a syringe barrel, upon engagement of needle hub 120 to a distal end of the syringe barrel.

While a Luer-type connector is shown and described, it is contemplated that any type of mechanical connector may be used, including and not limited to threads and bayonet-type structures.

As seen in FIGS. 5-21, safety shield 130 includes a pair of legs 130a, 130b and a foot or retention member 136. Each leg 130a, 130b includes a distal segment 132 and a proximal segment 134 connected to distal segment 132. The foot or retention member 136 is operatively connected to proximal segment 134 of each leg 130a, 130b.

As seen in FIGS. 5-8B, each distal segment 132 includes a body half 140, 142 each having a respective distal end 140a, 142a and a proximal end 140b, 142b. Distal end 140a of body half 140 defines a pair of spaced apart arms 141a, 141b extending from proximal end 140b thereof. A distal end of each arm 141a, 141b is connected to one another by a transverse strut or tooth 141c. Strut 141c functions to maintain the distance of arms 141a, 141b relative to one another as well as to close off a distal end of safety device 130 to minimize inadvertent contact with distal end 110a of syringe needle 110. A distal-most tip of each arm 141a, 141b may be rounded about at least one axis that is transverse to a longitudinal axis thereof.

Distal end 142a of body half 142 defines a pair of spaced apart arms 143a, 143b extending from proximal end 142b thereof. Arms 143a, 143b of distal end 142a of body half 142 are spaced apart an amount sufficient to overlie arms 141a, 141b of distal end 140a of body half 140, when safety shield 130 is assembled.

Proximal end 140b of body half 140 and proximal end 142b of body half 142 may each form a half-section of a substantially cylindrical, conical or rectangular body.

Distal segment 132 of each leg 130a, 130b further includes an inter-engaging feature 150 extending between and interconnecting body halves 140, 142 to one another. Inter-engaging feature 150 includes a first stem 152 extending from proximal end 142b of body half 142, between the pair of spaced apart arms 143a, 143b of distal end 142a of body half 142. Inter-engaging feature 150 further includes a needle guide 154 integrally formed with and hingedly connected to first stem 152 via a living hinge or a thinned-transition region 153. Needle guide 154 defines a lumen or passage 154a therethrough which is configured and dimensioned to slidably receive syringe needle 110 therein. Inter-engaging feature 150 still further includes a second stem 156 integrally formed with and hingedly connected to needle guide 154 via a living hinge or a thinned-transition region 155. A distal or free end 156a of second stem 156 defines a locking feature 156b configured and dimensioned to selectively engage a complementary locking feature 140c (see FIG. 7B) formed in an outer surface of body half 140 of distal segment 132.

Body halves 140, 142 of distal segment 132 of each leg 130a, 130b define a longitudinal channel 147 (see FIG. 6), which extends along the length thereof. Channel 147 defined by body halves 140, 142 is dimensioned and configured to receive a length of syringe needle 110 therein.

With continued reference to FIGS. 5-8B, each proximal segment 134 of each leg 130a, 130b of safety shield 130 includes a body half 160, 162 each having a distal end 160a, 162a and a proximal end 160b, 162b. Body halves 160, 162 of proximal segments 134 of each leg 130a, 130b define a longitudinal channel 167 (see FIG. 6), which extends along the length thereof. Channel 167 defined by body halves 160, 162 is dimensioned and configured to receive a length of syringe needle 110 therein. Channel 167 defined by body halves 160, 162 of proximal segment 134 is substantially aligned with channel 147 defined by body halves 140, 142 of distal segment 132.

Figure 5:
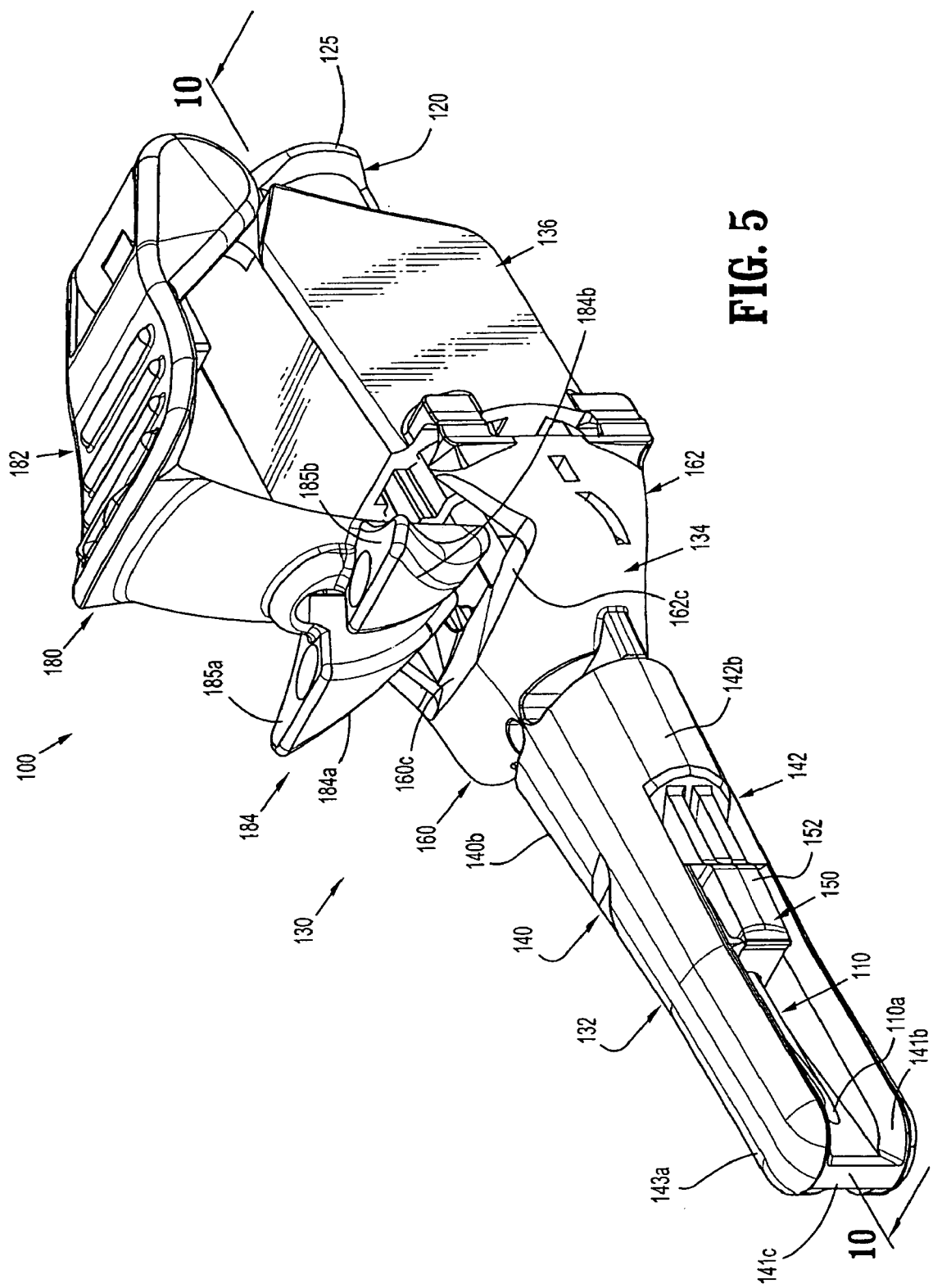
FIG. 5 is a perspective view of a safety device according to another embodiment of the present disclosure, shown in a first condition.

As seen in FIGS. 5, 6 and 7A, each body half 160, 162 defines a camming surface 160c, 162c formed substantially in an outer, top surface of proximal end 160b, 162b thereof. As will be discussed in greater detail below, camming surfaces 160c, 162c are each configured to operatively engage a camming member 184 of a trigger mechanism 180. Each body half 160, 162 further defines a shoulder, ledge or lip 160d, 162d formed below a respective camming surface 160c, 162c.

As seen in FIGS. 6 and 7A, a proximal end 140a of body half 140 of leg 130a is hingedly connected to a distal end 160a of body half 160 of leg 130a by a hinge member 161a. Likewise, a proximal end 142b of body half 142 of leg 130b is hingedly connected to a distal end 162a of body half 162 of leg 130b by a hinge member 161b. Hinge members 161a, 161b can be formed as separate matable components formed in or extending from respective body halves of each leg 130a, 130b, or can be formed as a thinned transition region and act as a living hinge which is integrally formed between respective body halves of each leg 130a, 130b.

As seen in FIGS. 6 and 7A, retention member 136 of safety shield 130 is monolithically or integrally formed with proximal segment 134 and is hingedly connected to body halves 160, 162 of proximal segment 134 of each leg 130a, 130b by thinned transition regions or living hinges 163a, 163b. Alternately, retention member 136 and body halves 160, 162 of proximal segment 134 of each leg 130a, 130b may be formed separately and pivotally attached to one another with a separate hinge member.

As seen in FIGS. 5, 6, 7C, 7D, 8A and 8B, safety shield 130 further includes a trigger mechanism 180 supported on retention member 136, and selectively, operatively associated with body halves 160, 162 of proximal segment 134 of each leg 130a, 130b. Trigger mechanism 180 includes a lever 182 pivotably attached at one 182a end thereof to retention member 136, and a second end 182b disposed over or extending over body halves 160, 162 of proximal segment 134 of each leg 130a, 130b. Attachment end 182a includes at least one pin member 188 configured to engage a complementary recess 136a formed in retention member 136. In particular, pin member 188 and recess 136a of retention member 136 are configured so as to limit the degree or amount of rotation of trigger mechanism 180 relative to retention member 136. After use, the pin member 188 of trigger mechanism 180 can be separated from recess 136a to remove trigger mechanism 180 from retention member 136.

Figure 7C:
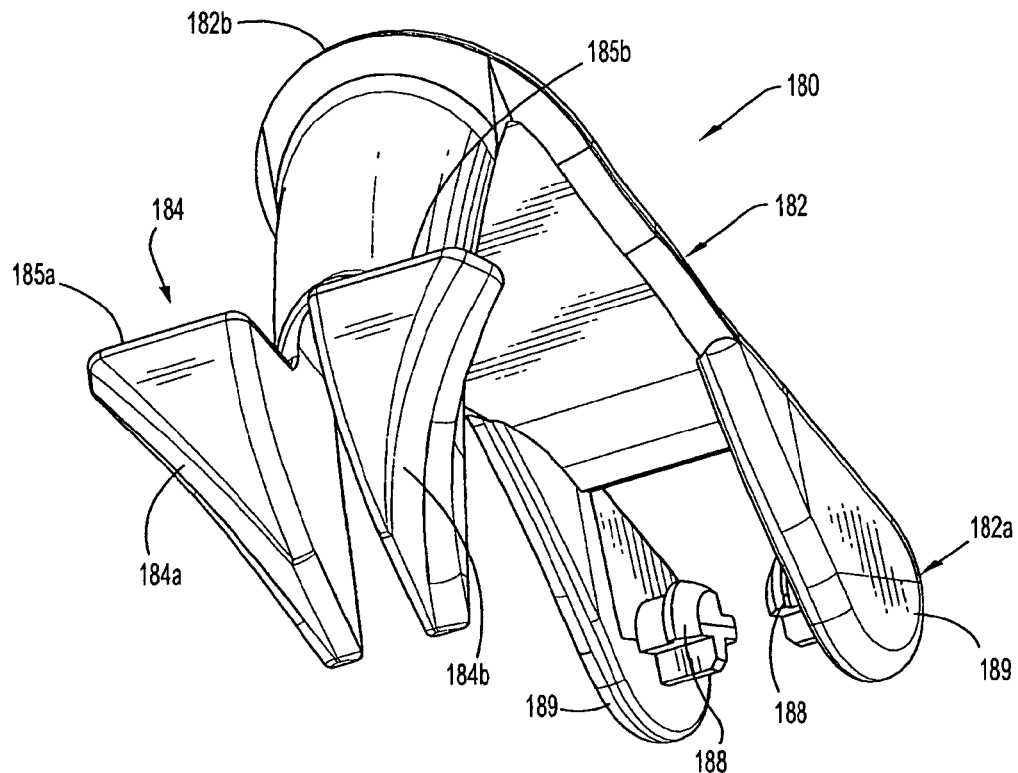
FIG. 7C is a front, bottom perspective view of a trigger mechanism of the safety device of FIGS. 5 and 6.
Figure 7D:
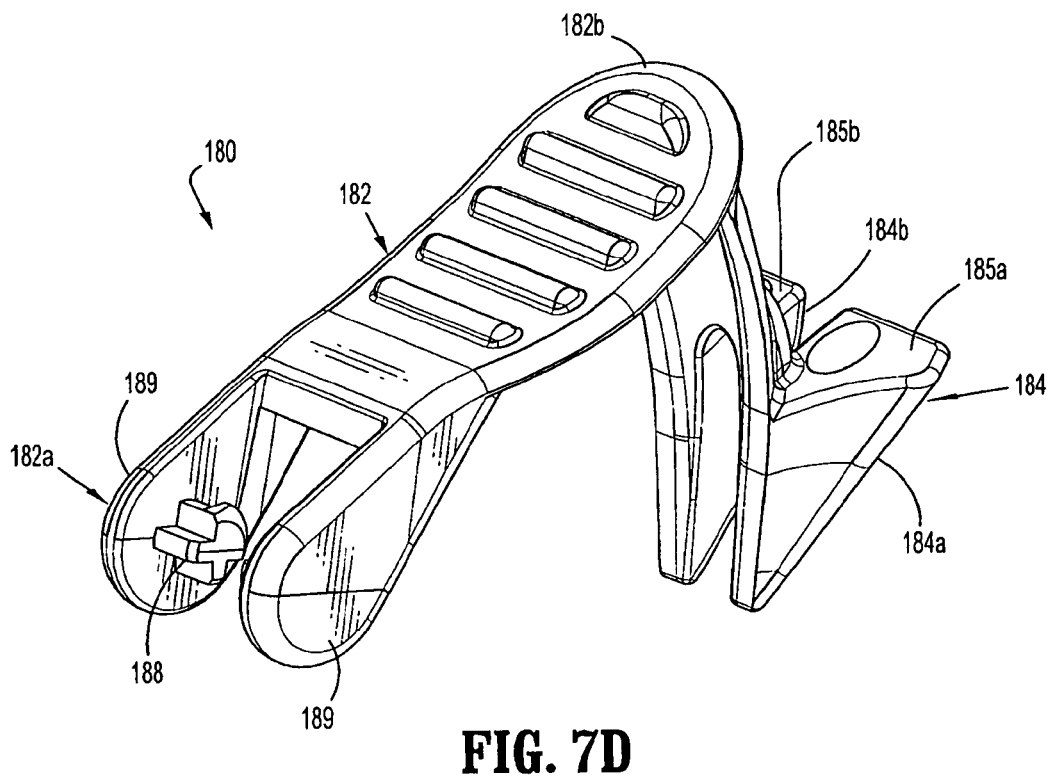
FIG. 7D is a rear, top perspective view of the trigger mechanism of FIG. 7C.

As seen in FIGS. 7C and 7D, pin members 188 may extend from an inner surface of a respective ear 189 of attachment end 182a. It is contemplated that each ear 189 may be fabricated from a resilient material having a sufficient flexibility so as to enable ears 189 to deflect away from one another during attachment and detachment of trigger mechanism 180 to safety shield 130, and having a sufficient stiffness so as to securely maintain trigger mechanism 180 connected to safety shield 130 during use thereof.

Trigger mechanism 180 includes a camming member 184 extending from second end 182b of lever 182, in a direction toward body halves 160, 162 of proximal segment 134 of each leg 130a, 130b. Camming member 184 of trigger mechanism 180 includes a pair of spaced apart cam portions or teeth 184a, 184b which are each configured and dimensioned to selectively engage a respective camming surface 160c, 162c of body halves 160, 162 of proximal segment 134 of each leg 130a, 130b. Cam portions 184a, 184b are spaced apart from one another an amount sufficient to receive and/or accommodate syringe needle 110 therebetween. Each cam portion 184a, 184b includes a substantially tapered profile having a narrow distal end and an enlarged proximal engaging surface 185a, 185b, respectively.

In operation, as will be described in greater detail below, cam portions 184a, 184b of camming member 184 are configured and dimensioned to press against respective camming surfaces 160c, 162c to force body halves 160, 162 of proximal segment 134 of each leg 130a, 130b apart from one another whilst not obstructing or interfering with the passage of syringe needle 110.

As seen in FIGS. 6 and 7A, a biasing member 186 is operatively disposed between retention member 136 and lever 182 of trigger mechanism 180. Biasing member 186 is configured and adapted to maintain camming member 184 spaced away from camming surfaces 160c, 162c of body halves 160, 162 of proximal segment 134 of each leg 130a, 130b.

As seen in FIG. 6, safety shield 130 further includes a pair of biasing members 190a, 190b each operatively inter connecting retention member 136 and a respective body half 160, 162 of proximal segment 134 of each leg 130a, 130b. Biasing members 190a, 190b are configured to maintain body halves 160, 162 of proximal segment 134 substantially in contact with one another and/or substantially in a first condition. In particular, each biasing member 190a, 190b may be a resilient rod, e.g., nitinol, having a first end extending into and supported in retention member 136 and a second end extending into and supported in a respective body half 160, 162 of proximal segment 134 of each leg 130a, 130b.

As seen in FIGS. 6-8B, the joining of body halves 140, 142 of legs 130a, 130b to one another to form distal segment 132 of safety shield 130 is shown and described below. As seen in FIGS. 6-8B and particularly FIGS. 8A and 8B, free end 156a of second stem 156 of inter-engaging feature 150 is threaded or passed through arms 141a, 141b of body half 140. With free end 156a of second stem 156 threaded or passed through arms 141a, 141b of body half 140, locking feature 156b of free end 156a of second stem 156 is connected to the complementary locking feature 140c (see FIG. 7B) formed in the outer surface of body half 140. In so doing, needle guide 154 is disposed substantially along a longitudinal axis of safety shield 130. In particular, lumen 154a of needle guide 154 is substantially axially aligned with lumen 122a of needle support 122 when safety shield 130 is coupled to needle hub 120. With body halves 140, 142 of legs 130a, 130b joined to one another via inter-engaging feature 150, syringe needle 110 may be passed through lumen 154a of needle guide 154.

Referring to FIGS. 9 and 10, in its first or shielded position, safety shield 130 is configured such that body halves 140, 142 of distal segment 132 of each leg 130a, 130b and body halves 160, 162 of proximal segment 134 of each leg 130a, 130b are either axially aligned with one another or are substantially parallel with a longitudinal axis of syringe needle 110. In the extended position, camming member 184 of trigger mechanism 180 overlies camming surfaces 160c, 162c of body halves 160, 162 of proximal segment 134.

Safety shield 130 of safety device 100 is configurable to a primed position, wherein the hinge members 161a, 161b connecting distal segments 132 of each leg 130a, 130b to proximal segments 134 of each leg 130a, 130b are splayed outwardly of each other (FIG. 13) and distal segments 132 of each leg 130a, 130b separate in a scissor-like fashion. In so doing, distal end 110a of syringe needle 110 is exposed for use.

To configure safety shield 130 of safety device 100 to the primed position, as depicted in FIGS. 11-16, lever 182 of trigger mechanism 180 is pressed downwardly (i.e., towards syringe needle 110), as indicated by arrow "A", thereby pressing cam portions 184a, 184b of camming member 184 of trigger mechanism 180 against respective camming surfaces 160c, 162c of body halves 160, 162 of proximal segment 134 of each leg 130a, 130b. As cam portions 184a, 184b of camming member 184 press against respective camming surfaces 160c, 162c of body halves 160, 162, hinge members 161a and 161b of body halves 160, 162 are moved apart from one another (i.e., away from syringe needle 110), as indicated by arrows "B". In so doing, needle guide 154 is translated along a length of syringe needle 110, e.g., in a proximal direction along syringe needle 110. Lever 182 of trigger mechanism 180 is pressed in the direction of arrow "A" until proximal engaging surfaces 185a, 185b of camming member 184 move beneath or snap-under respective shoulders 160d, 162d of camming surfaces 160c, 162c of body halves 160, 162.

As lever 182 of trigger mechanism 180 is pressed in the direction of arrow "A", lever 182 acts on biasing member 186 to bias and/or flex biasing member 186. Additionally, as camming member 184 of trigger mechanism 180 acts on camming surfaces 160c, 162c of body halves 160, 162 to separate body halves 160, 162 from one another, respective biasing members 190a, 190b are each biased and/or flexed.

When in the primed position, as seen in FIG. 14, cam portions 184a, 184b of camming member 184 have a length sufficient to extend below a bottom-most surface of safety shield 130, in particular, retention member 136 and/or needle hub 120. This extension can be engaged by medical personnel and urged upwardly to effect de-support of shoulders 160d, 162d of camming surfaces 160c, 162c from engaging surfaces 185a and 185b of camming member 184 as will be discussed below.

Figure 11:
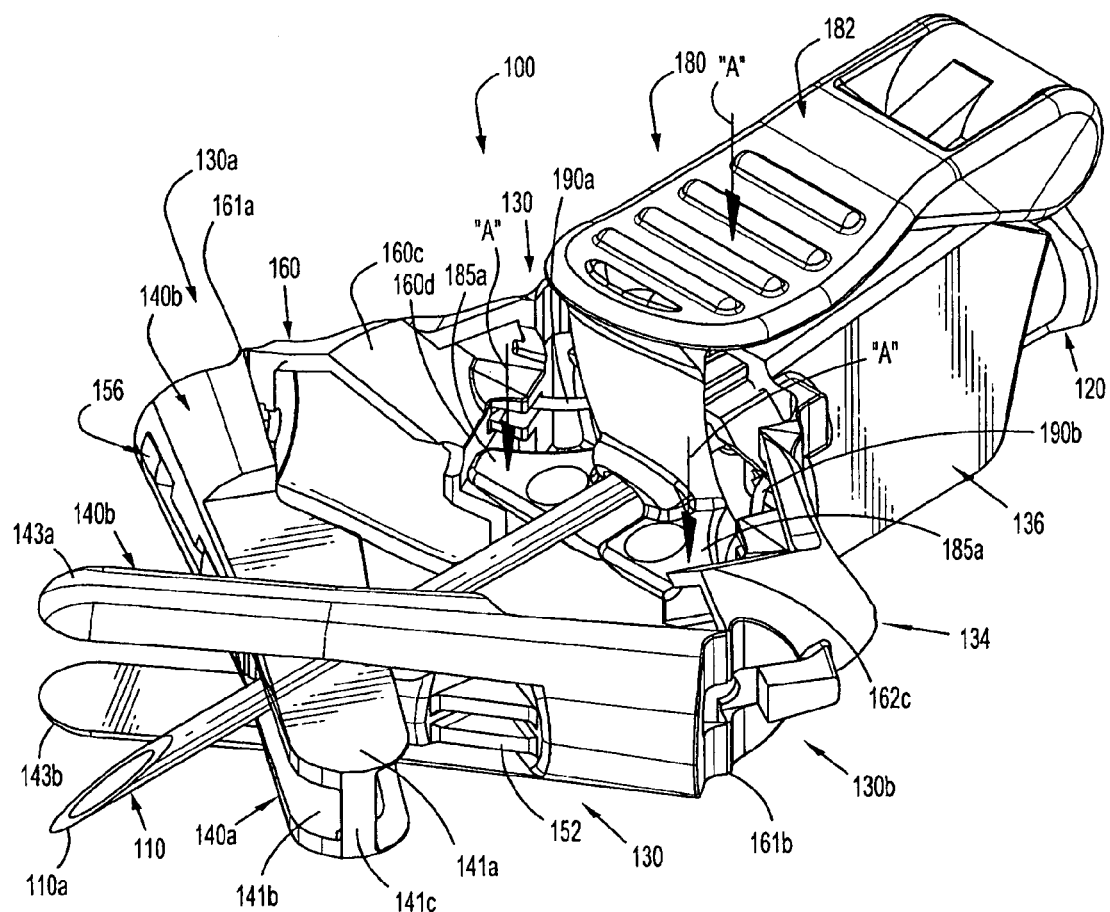
FIG. 11 is a perspective view of the safety device of FIGS. 5-10, illustrating the safety device being actuated to a primed condition.
Figure 12:
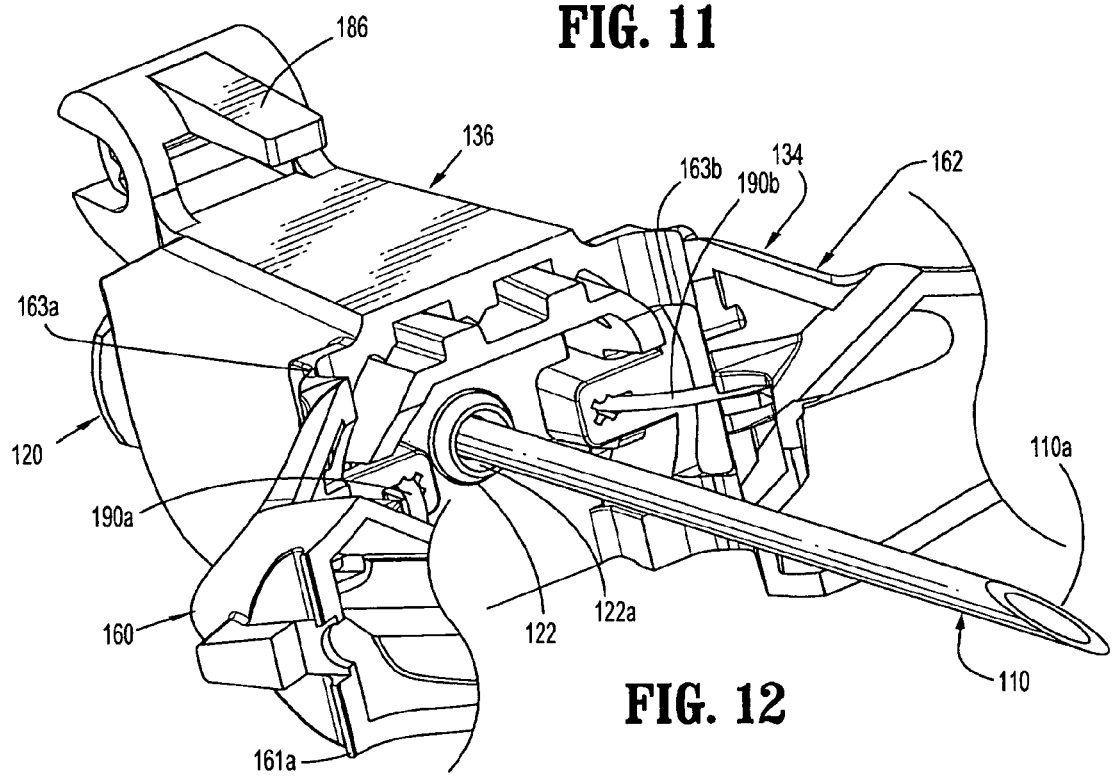
FIG. 12 is a perspective view, partially broken away, of the safety device of FIG. 11 with the trigger mechanism removed therefrom.
Figure 15:
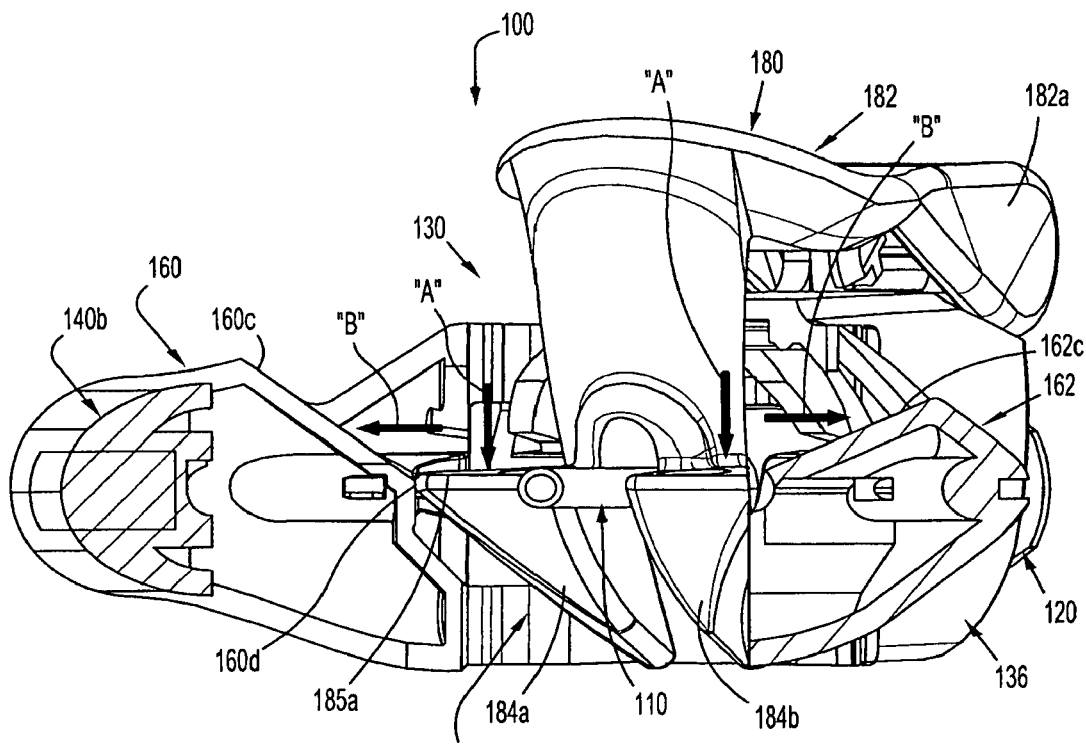
FIG. 15 is a cross-sectional view of the safety device of FIGS. 5-14, as taken through 15-15 of FIG. 13, illustrating the safety device in a configuration just prior to being fully primed.
Figure 16:
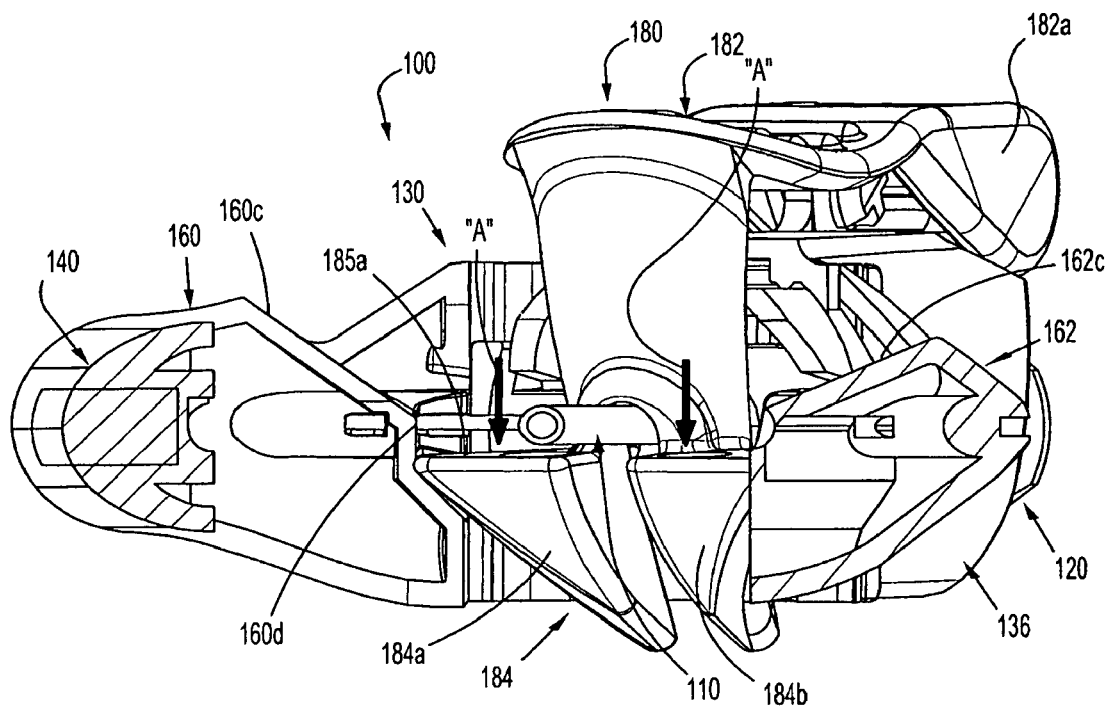
FIG. 16 is a cross-sectional view of the safety device of FIGS. 5-14, as taken through 15-15 of FIG. 13, illustrating the safety device in a configuration just following being fully primed.
Figure 17:
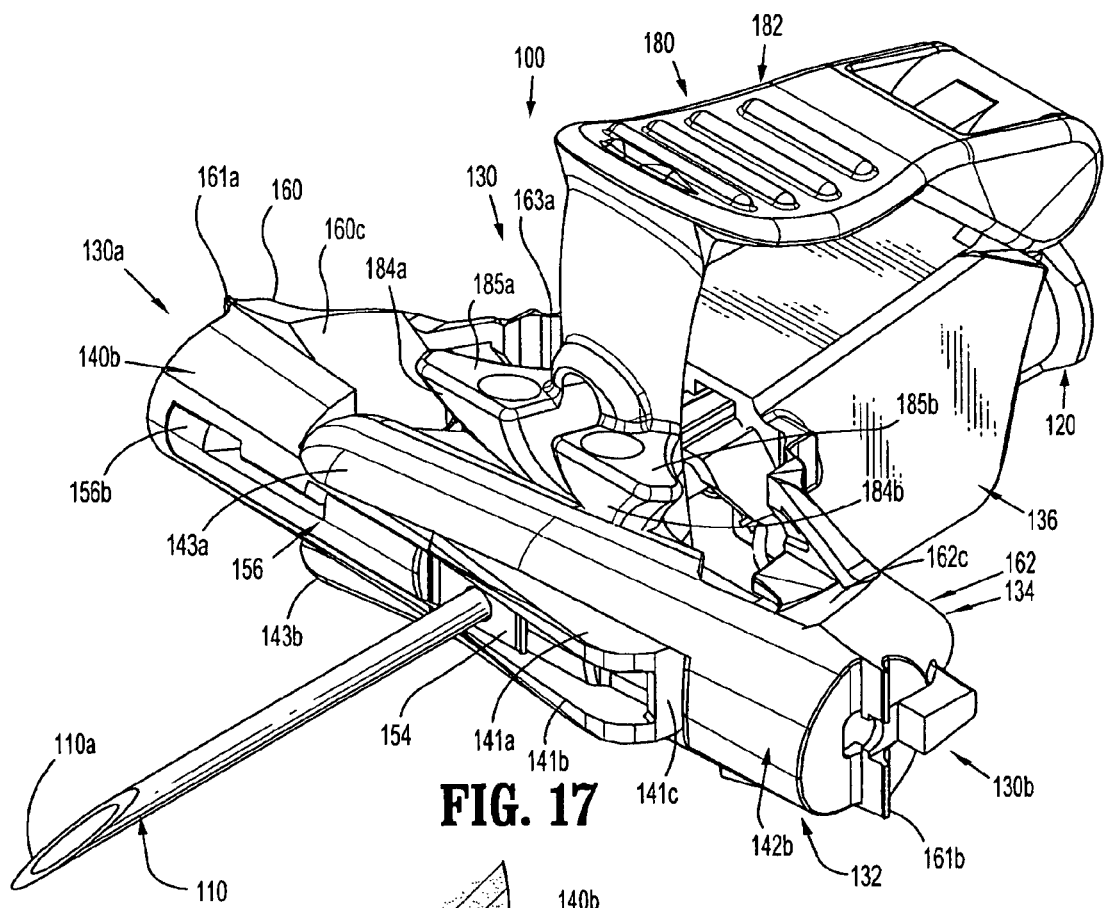
FIG. 17 is a perspective view of the safety device of FIGS. 5-16, illustrating the safety device in a fully actuated condition.
Figure 18:
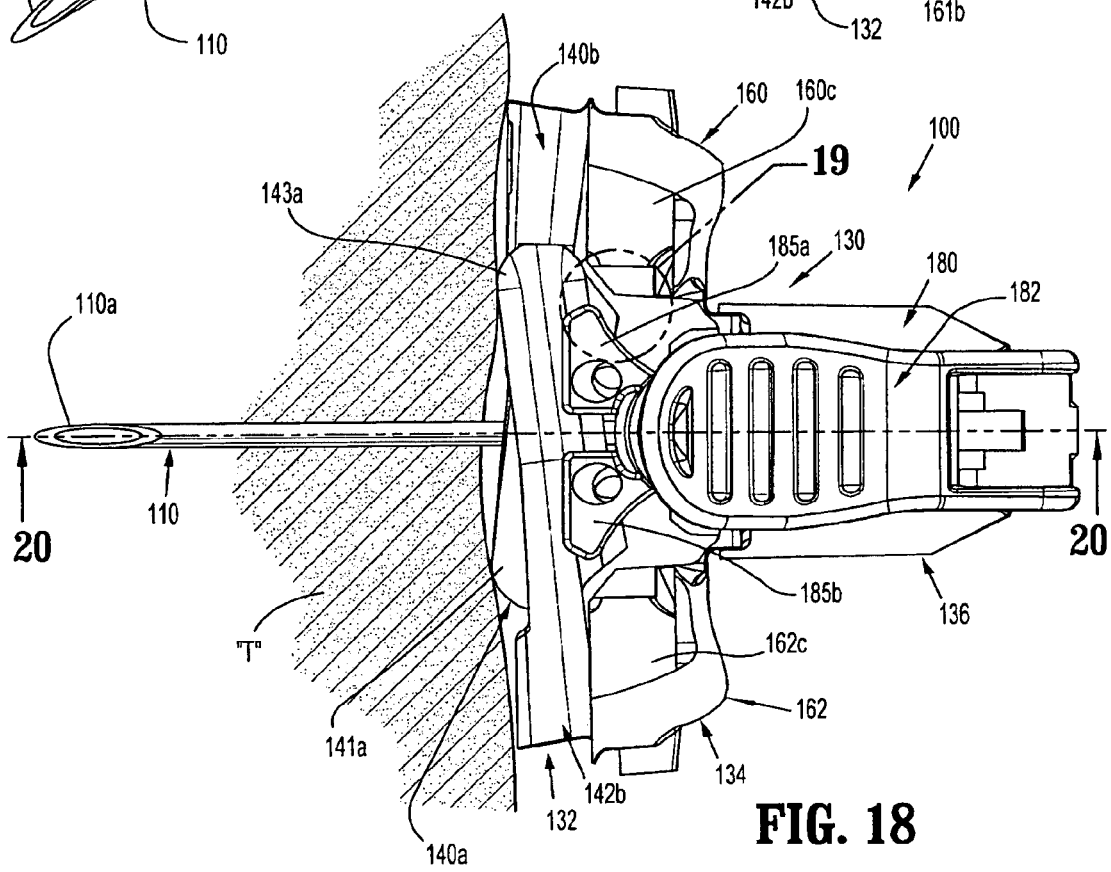
FIG. 18 is a top, plan view of the safety device of FIGS. 5-17, illustrating the safety device injected into tissue and in the fully actuated condition.
Figure 19:
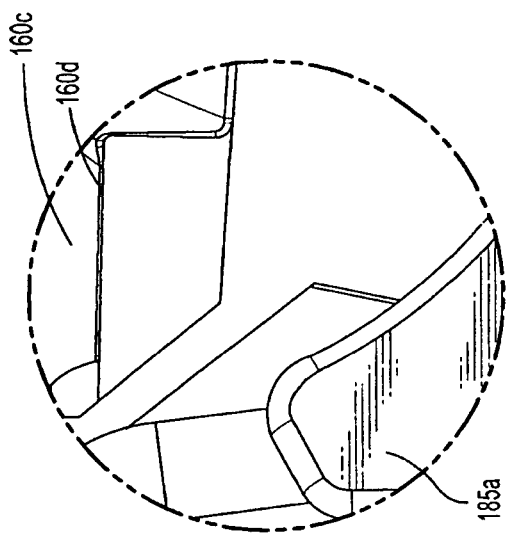
FIG. 19 is an enlarged view of the indicated area of detail of FIG. 18.
Figure 20:
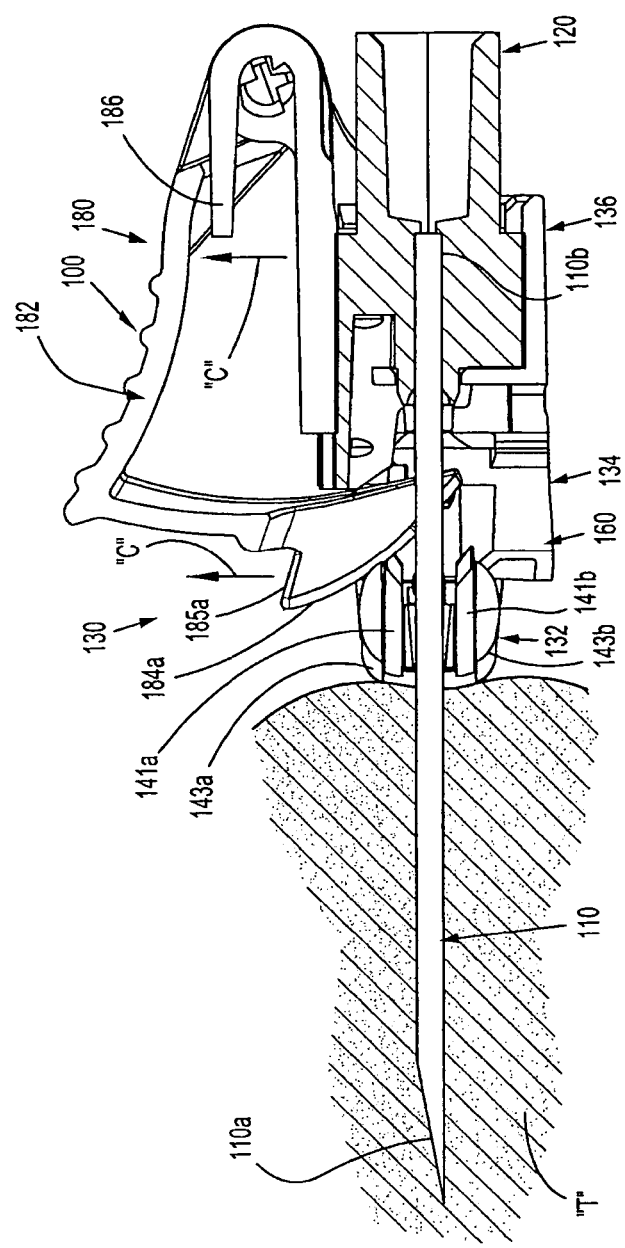
FIG. 20 is a longitudinal, cross-sectional view of the safety device of FIGS. 5-19, as illustrated injected in tissue as seen in FIG. 18.

In the primed position, safety device 100 may be used as any conventional medical needle to inject and withdraw blood from a subject, to withdraw medication from a vial, or the like. In particular, while safety device 100 is in the primed position, as shown in FIG. 11, any subsequently applied longitudinal forces acting on distal ends of arms 141a, 141b of body half 140 of distal segment 132 of each leg 130a, 130b and distal ends of arms 143a, 143b of body half 142 of distal segment 132 of each leg 130a, 130b, such as, during insertion of syringe needle 110 into tissue "T" (see FIG. 18), will cause said distal ends to move toward retention member 136. In so doing, as seen in FIGS. 17 and 18, body halves 160, 162 are moved or splayed further apart from one another by an amount which is at least sufficient to move respective shoulders 160d, 162d beyond proximal engaging surfaces 185a, 185b of camming member 184 (see FIG. 19). As so positioned, biasing member 186 is free to return to its unbiased or un-flexed condition, thereby urging lever 182 of trigger mechanism 180 in the direction of arrow "C" (opposite to arrow "A") by an amount sufficient to move or clear engaging surfaces 185a, 185b of camming member 184 above shoulders 160d, 162 of body halves 160, 162.

Figure 21:
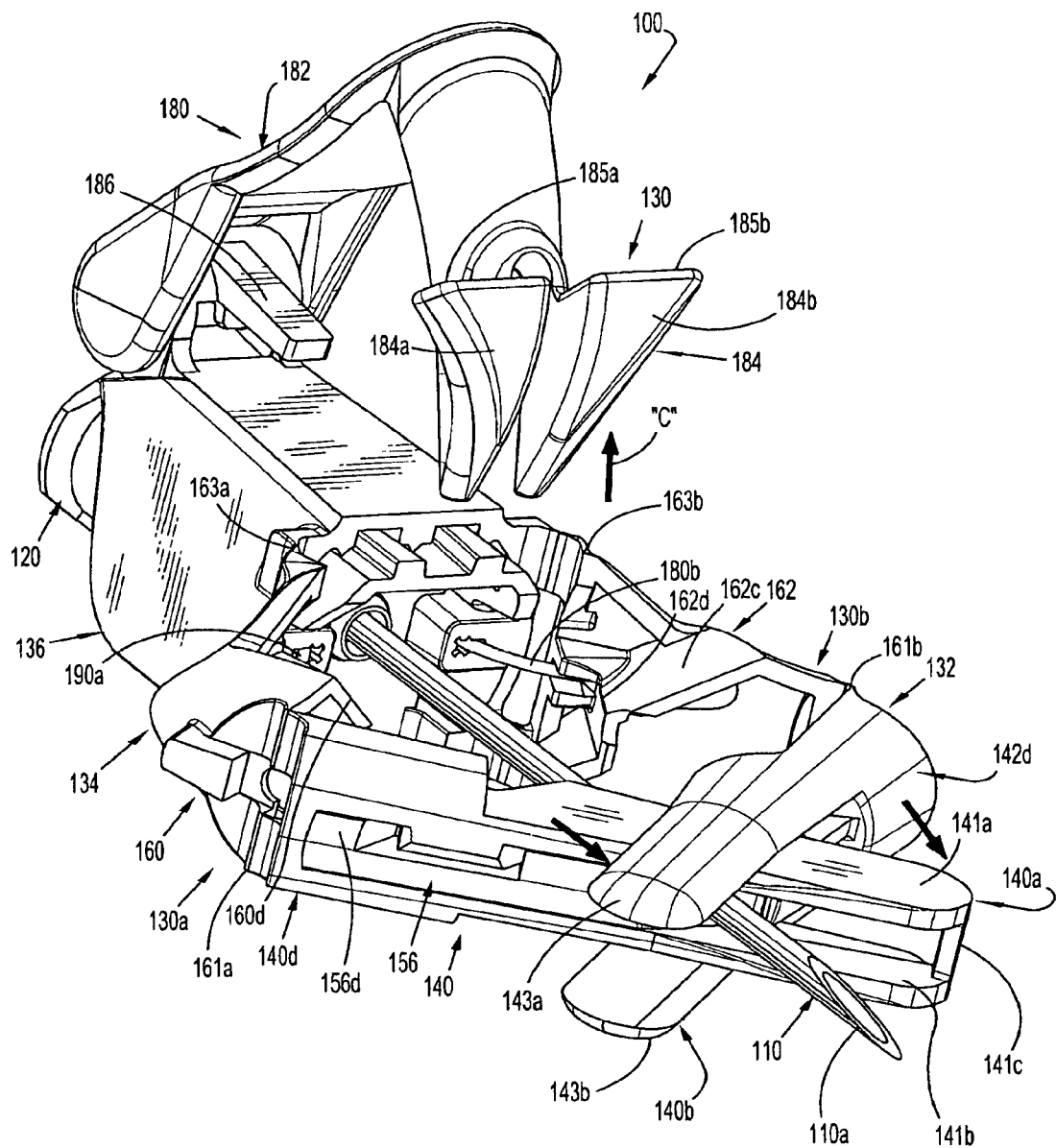
FIG. 21 is a perspective view of the safety device of FIGS. 5-20, illustrating a return of the safety device to the first condition when the safety device is withdrawn from the tissue.

Once engaging surfaces 185a, 185b of camming member 184 are moved above shoulders 160d, 162 of body halves 160, 162, as seen in FIG. 21, as safety device 100 is withdrawn from tissue "T", each biasing member 190a, 190b is free to return to an unbiased or un-flexed condition thereby approximating body halves 160, 162 of proximal segment 134 of each leg 130a, 130b towards one another. As body halves 160, 162 of proximal segment 134 of each leg 130a, 130b are approximated towards one another, body halves 140, 142 of distal segment 132 of each leg 130a, 130b are re-aligned with one another to thereby re-sheath distal end 110a of syringe needle 110.

Referring back to FIG. 14, in the event that the user to clinician desires to return safety shield 130 to the first condition, following priming of safety shield 130, the clinician may apply a force, substantially in the direction of arrow "D", on the free end of camming member 184 extending beneath the bottom-most surface of safety shield 130, in particular, retention member 136 and/or needle hub 120. In so doing, engaging surfaces 185a, 185b of camming member 184 urge against a surface of respective shoulders 160d, 162d of body halves 160, 162, causing body halves 160, 162 to move apart and allow for engaging surfaces 185a, 185b of camming member 184 to move above or clear shoulders 160d, 162d of body halves 160, 162. Once engaging surfaces 185a, 185b of camming member 184 have moved above or cleared shoulders 160d, 162d of body halves 160, 162, as described above, each biasing member 190a, 190b is free to return to an unbiased or un-flexed condition thereby approximating body halves 160, 162 of proximal segment 134 of each leg 130a, 130b towards one another and thereby re-sheath syringe needle 110.

While safety device 100 is in the first and sheathed configurations, distal end 110a of syringe needle 110 is shielded and thus a clinician is protected from inadvertent or accidental sticking by distal end 110a of syringe needle 110 once use of syringe needle 110 of safety device 100 has been completed.

Figure 22:
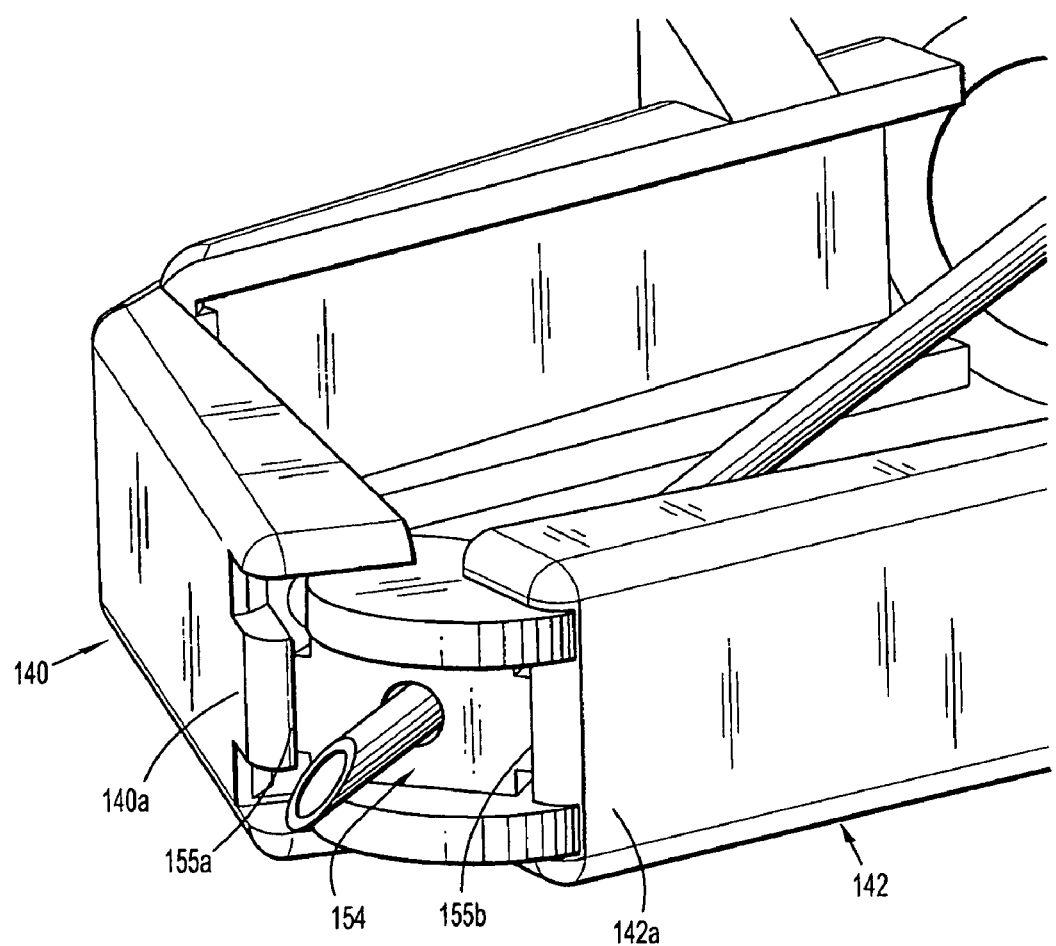
FIG. 22 is a perspective view of an alternate embodiment of a safety shield of the present disclosure, shown in a partially splayed condition.

Turning now to FIG. 22, as seen therein, in an alternate embodiment of safety shield 130, needle guide 154 may be hingedly connected between distal end 140a of body half 140 and distal end 142a of body half 142. In particular, needle guide 154 may be connected therebetween by a pair of living hinges or thinned-transition regions 155a, 155b.

Figure 23:
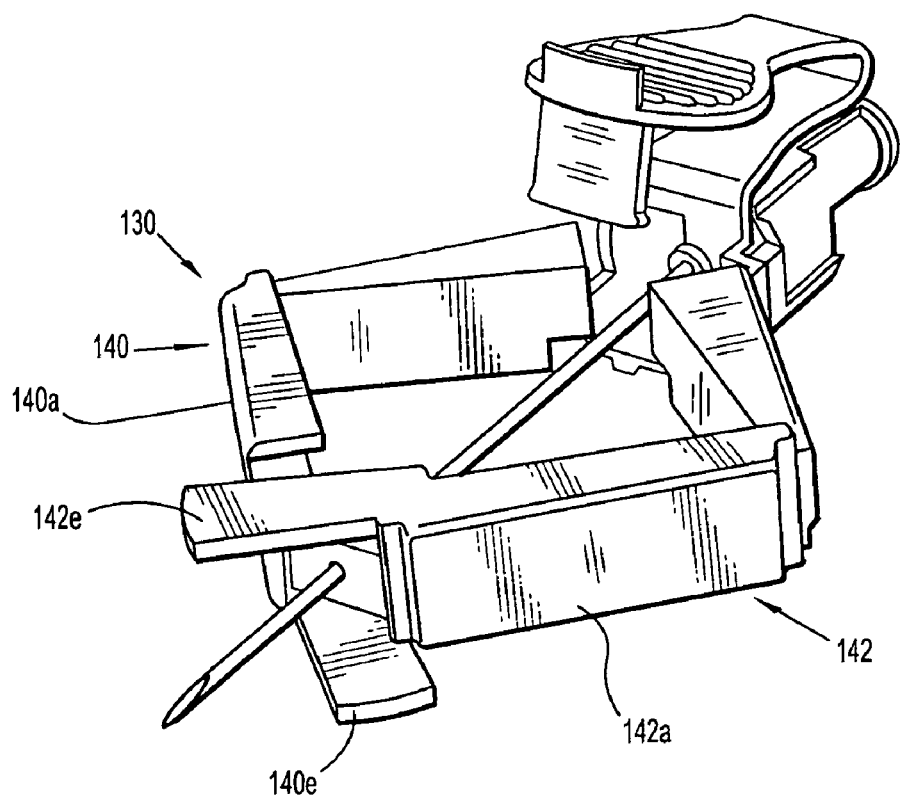
FIG. 23 is a perspective view of another alternate embodiment of a safety shield of the present disclosure, shown in a partially splayed condition.

As seen in FIG. 23, in an embodiment, safety shield 130 may include a wall 140e extending distally from a top surface and/or a bottom surface of distal end 140a of body half 140 and/or a wall 142e extending distally from a top surface and/or a bottom surface of distal end 142a of body half 142.

Figure 24:
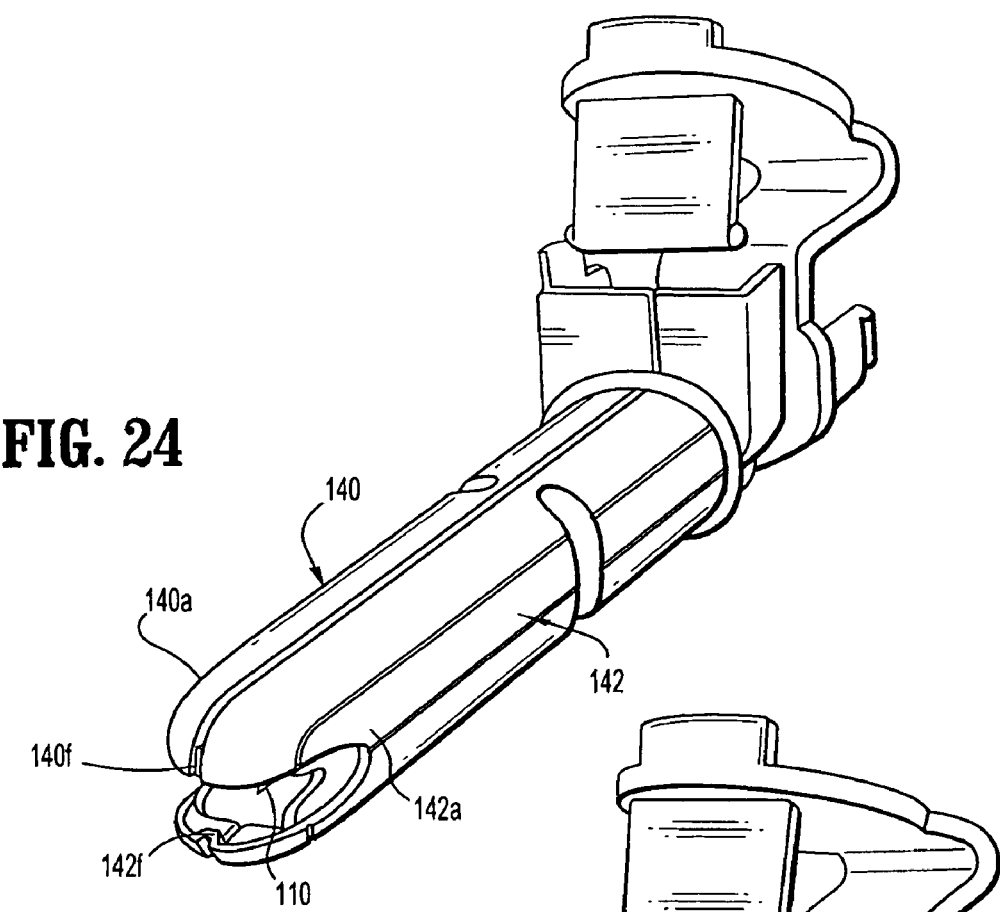
FIG. 24 is a perspective view of yet another alternate embodiment of a safety shield of the present disclosure, shown in a first condition.
Figure 25:
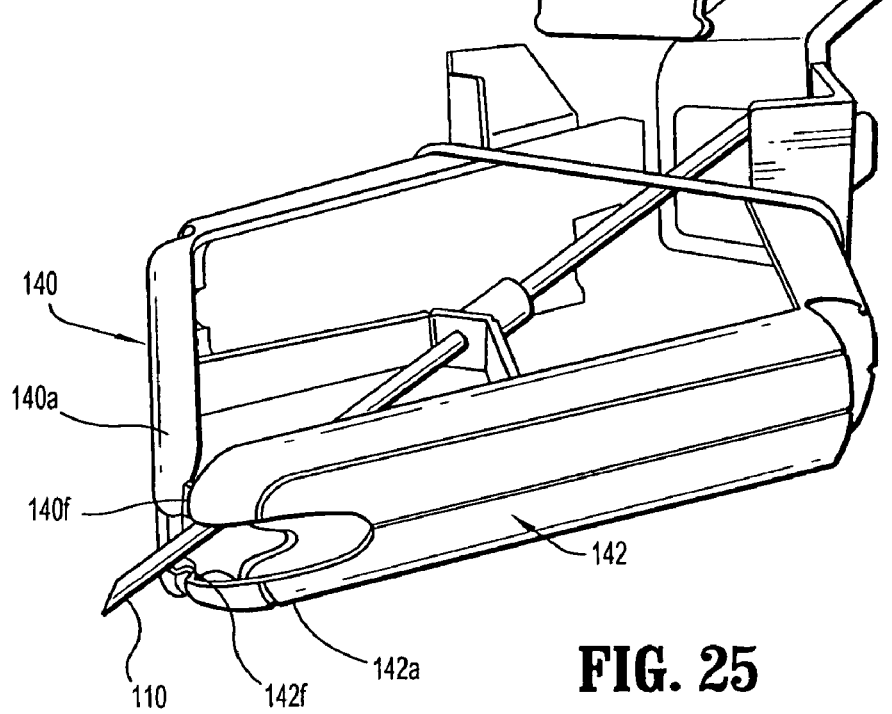
FIG. 25 is a perspective view of the safety shield of FIG. 24, shown in a partially splayed condition.

As seen in FIGS. 24 and 25, in an embodiment, distal end 140a of body half 140 and distal end 142a of body half 142 may be joined to one another via a pair of living hinges or thinned-transition regions 140f, 142f. It is contemplated that living hinges 140f, 142f are spaced apart and respectively located above and below needle syringe 110.

Figure 26:
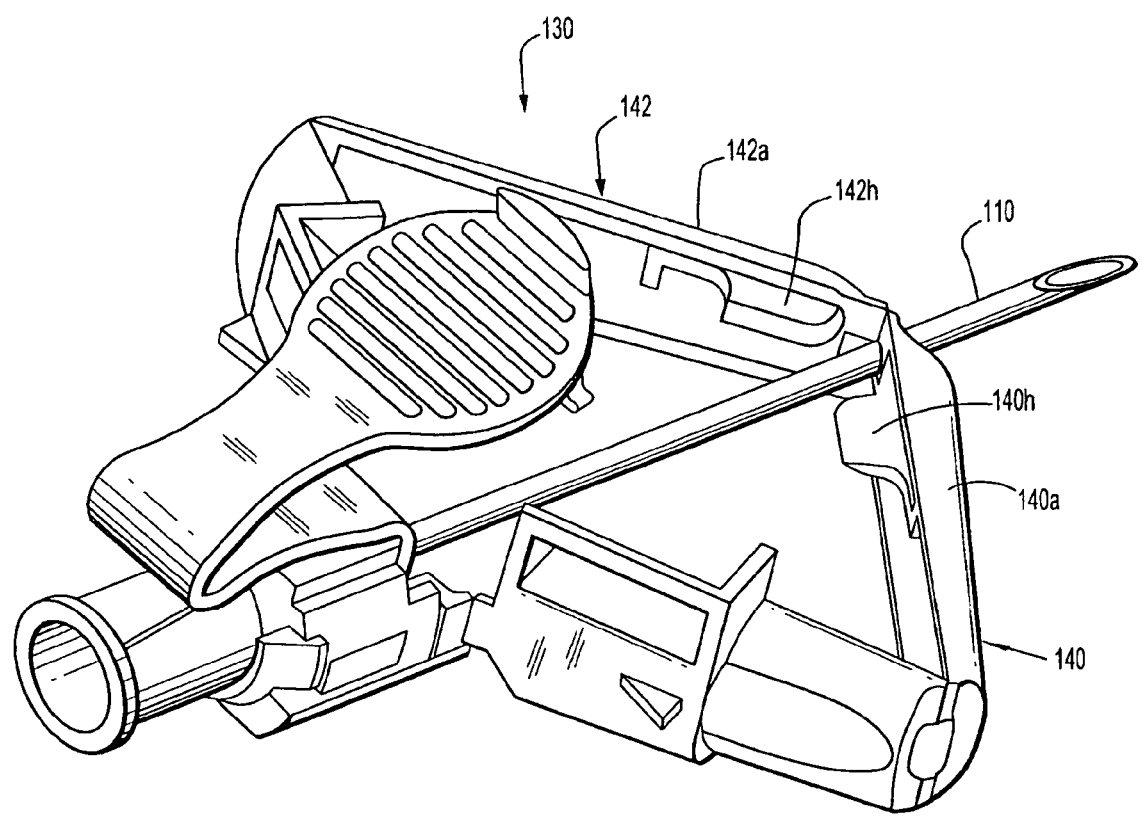
FIG. 26 is a perspective view of a further alternate embodiment of a safety shield of the present disclosure, shown in a partially splayed condition.

As seen in FIG. 26, each of distal end 140a of body half 140 and distal end 142a of body half 142 may include a respective guide wall 140h, 142h projecting from an inner surface thereof. In an embodiment, guide walls 140h, 142h may straddle needle syringe 110, thereby providing support thereto as safety shield 130 is splayed.

Figure 27:
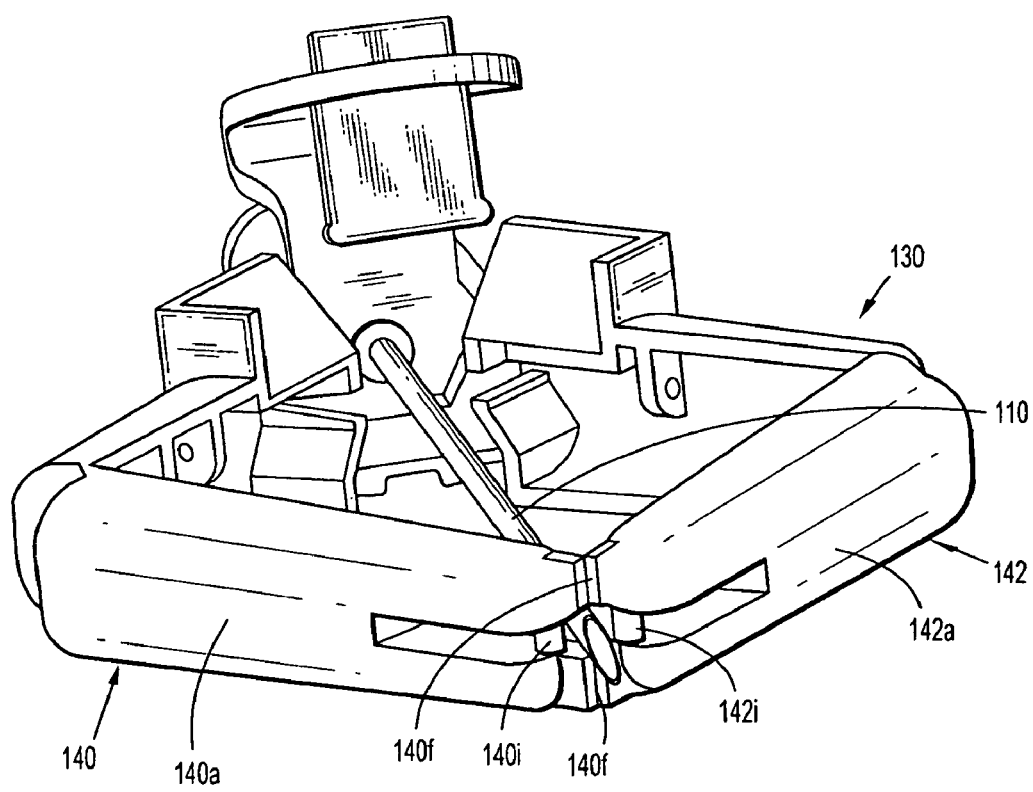
FIG. 27 is a perspective view of still a further alternate embodiment of a safety shield of the present disclosure, shown in a partially splayed condition.

As seen in FIG. 27, in an embodiment, each of distal end 140a of body half 140 and distal end 142a of body half 142 may include a respective guide pin 140i, 142i extending between respective arms 141a, 141b and arms 142a, 143b.

Guide pins 140i, 142i, together with living hinges 140f, 142f, function to substantially surround needle syringe 110 and provide support thereto as safety shield 130 is splayed.

Figure 28:
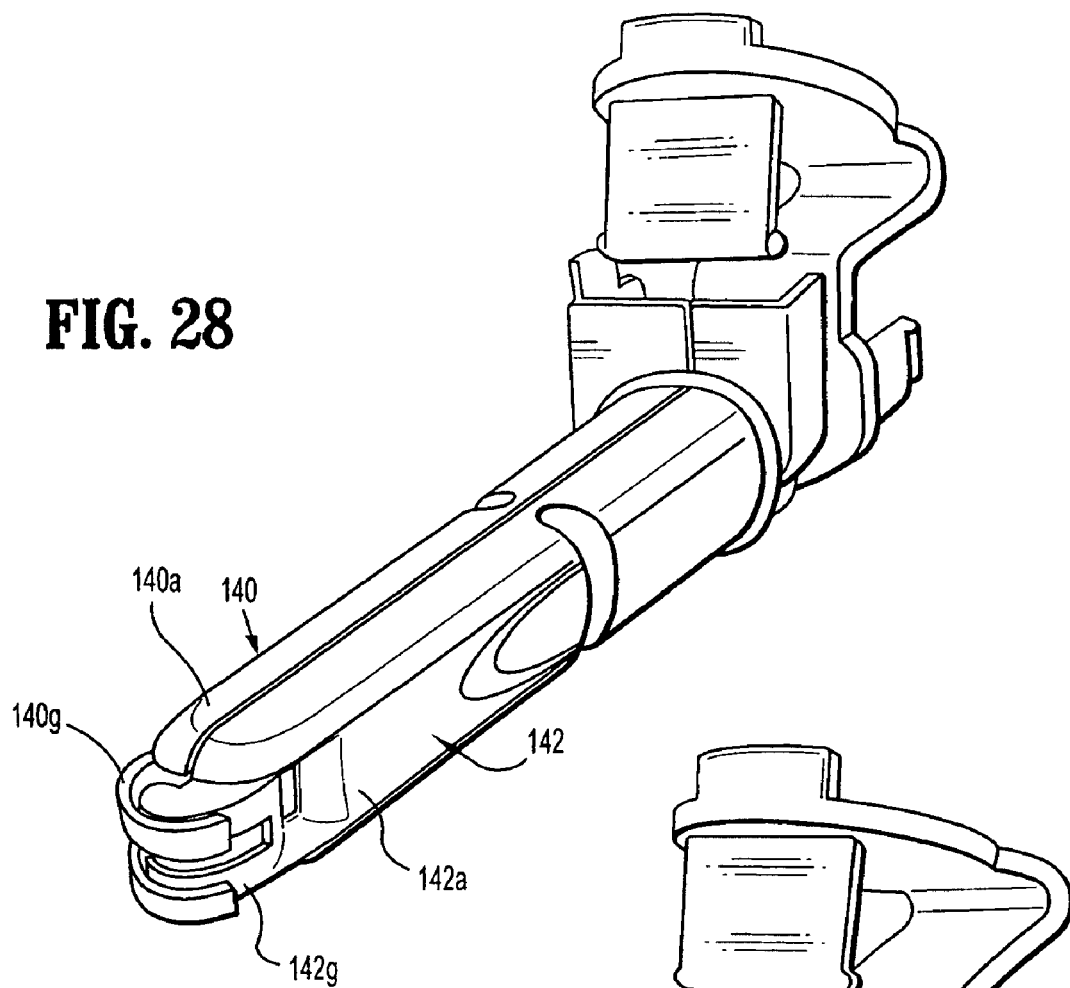
FIG. 28 is a perspective view of an alternate embodiment of a safety shield of the present disclosure, shown in a first condition.
Figure 29:
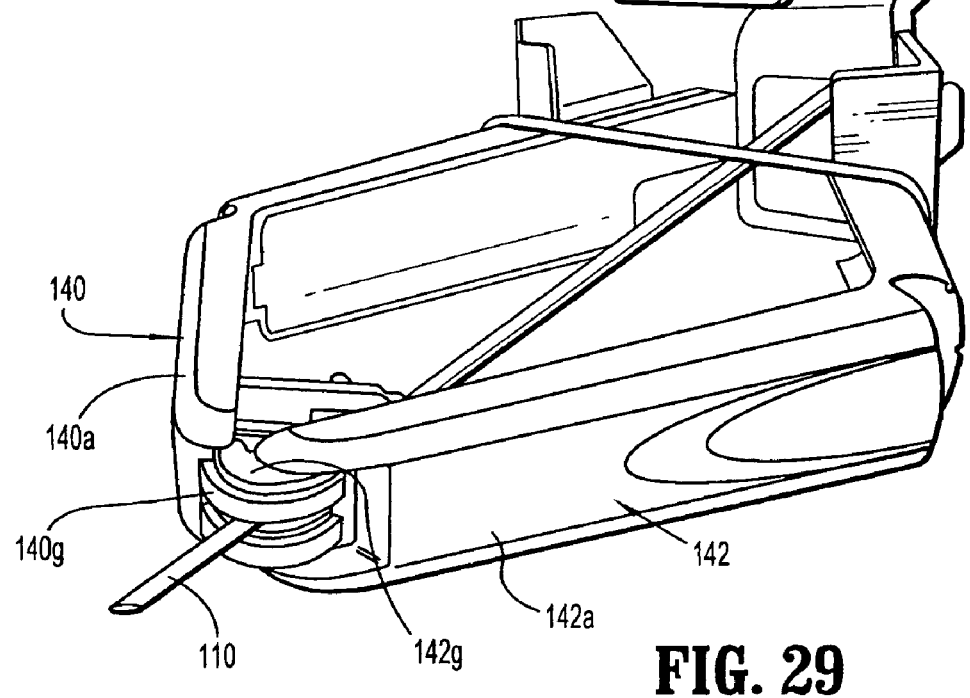
FIG. 29 is a perspective view of the safety shield of FIG. 28, shown in a partially splayed condition.

Alternatively, as seen in FIGS. 28 and 29, distal end 140a of body half 140 and distal end 142a of body half 142 may be joined to one another via a complementary pair of inter-engaging claws 140g, 142g. It is contemplated that each claw 140g, 142g defines a gap or space to accommodate needle syringe 110 therebetween.

Figure 30:
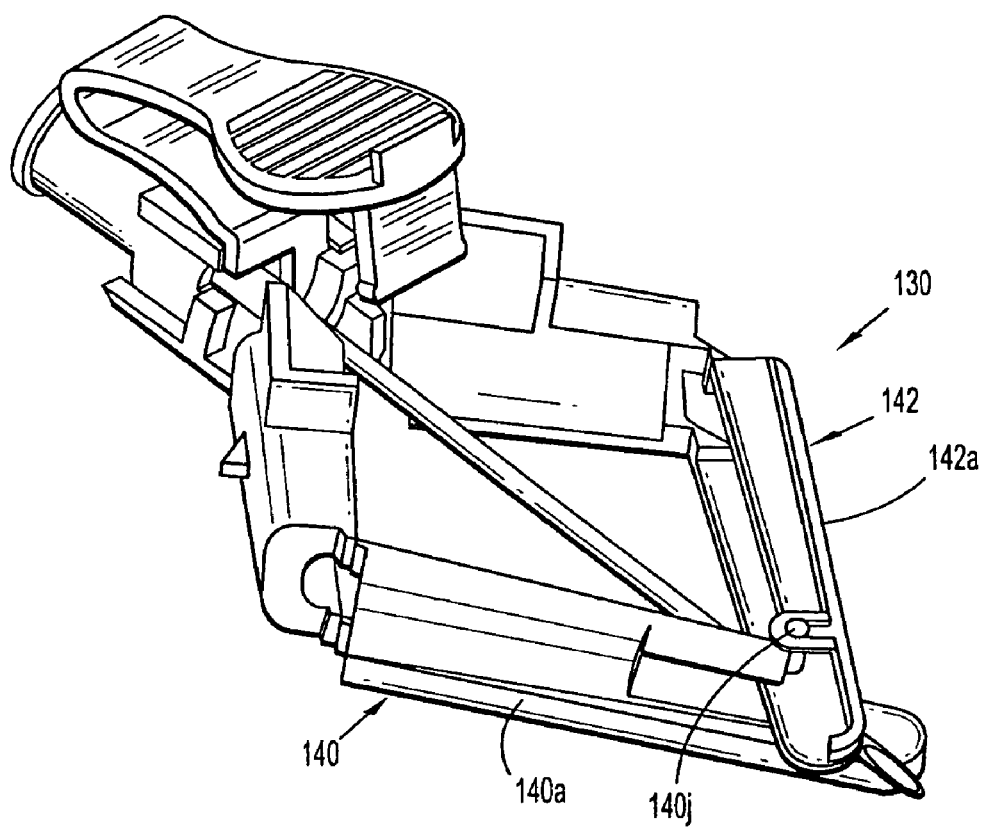
FIG. 30 is a perspective view of another alternate embodiment of a safety shield of the present disclosure, shown in a partially splayed condition.

Alternatively, as seen in FIG. 30, distal end 140a of body half 140 and distal end 142a of body half 142 may be joined to one another via a pivot pin 140j (only the pivot pin of body half 140 being shown) extending through features of body half 140 and body half 142.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A medical safety device comprising:
    a needle hub having a needle supported thereon; and
    a safety shield operatively mounted on the needle hub, the safety shield including a pair of spaced legs and a foot member, each of the legs having a distal segment and a proximal segment, each of the proximal segments having a proximal end hingedly attached to the foot member and a distal end hingedly attached to the distal segment at a hinge member, each proximal segment including a camming surface, the safety shield further including a trigger supported on the foot member, the trigger including a camming member and being movable to move the camming member into engagement with the camming surfaces of the proximal segments to effect movement of the legs from a first position in which the distal ends of the distal segments shield a distal end of the needle to a second position in which the distal end of the needle is at least partially exposed, wherein the camming member of the trigger includes a pair of spaced cam portions, each of the cam portions being configured to engage one of the camming surfaces of the proximal segments, wherein the trigger is removably secured to the foot member such that the trigger can be removed from the foot member to prevent movement of the legs from the first position to the second position.

2. A medical safely device according to claim 1, wherein each of the camming portions includes a substantially tapered profile having a narrow distal end and an enlarged proximal end.

3. A medical safety device according to claim 2, wherein the proximal end of each camming portion defines an engaging surface for engaging a shoulder on one of the proximal segments.

4. A medical device according to claim 2, wherein the distal end of at least one of the camming portions extends below a bottom-most surface of the safety shield.

5. A medical safety device according to claim 1, further including a biasing member configured to urge the legs to the first position.

6. A medical safety device according to claim 5, wherein the biasing member includes a piece of spring wire engaging each leg, each piece of spring wire having a first end secured to the foot member and a second end extending along at least a portion of a respective leg.

7. A medical safety device according to claim 1, wherein in the first position, the distal and proximal segments are substantially linearly aligned with the hinge member of each leg positioned adjacent the needle such that when a force is applied to the distal end of the distal segments, the legs are retained in the first position.

8. A medical safety device according to claim 1, wherein the camming member of the trigger and the camming surfaces of the proximal segments are positioned and configured such that movement of the camming member of the trigger into engagement with the camming surfaces of the proximal segments splays the hinge member of each of the legs outwardly to retract the distal end of each of the distal segment proximally towards the foot member.

9. A medical safety device according to claim 1, wherein each of the legs defines a channel dimensioned to receive the needle.

10. A medical safety device according to claim 1, wherein the trigger is pivotally secured to the foot member.

11. A medical device according to claim 1, further including an interengaging element positioned between and interconnecting the distal segments of the legs, the interengaging element including a needle guide defining a lumen dimensioned to slidably receive the needle.

12. A medical safety device according to claim 1, further including a biasing member positioned to urge the trigger out of engagement with the camming surfaces of the proximal segments.

13. A medical safety device according to claim 1, wherein the camming member of the trigger includes at least one engaging surface and the camming surfaces of the proximal segments include at least one shoulder, the at least one engaging surface being movable into engagement with the at least one shoulder to retain the trigger in engagement with the proximal segments and retain the legs in the second position.

14. A medical safety device comprising:
    a needle hub having a needle supported thereon; and
    a safety shield operatively mounted on the needle hub, the safety shield including a pair of spaced legs and a foot member, each of the legs having a distal segment and a proximal segment, each of the proximal segments having a proximal end hingedly attached to the foot member and a distal end hingedly attached to the distal segment at a hinge member, each proximal segment including a camming surface, the safety shield further including a trigger supported on the foot member, the trigger including a camming member and being movable to move the camming member into engagement with the camming surfaces of the proximal segments to effect movement of the legs from a first position in which the distal ends of the distal segments shield a distal end of the needle to a second position in which the distal end of the needle is at least partially exposed, wherein the camming member is configured to extend below a bottom surface of the foot member when pressed into engagement with the camming surfaces of the proximal segments, wherein the camming member includes a pair of spaced cam portions which define a channel dimensioned to receive the needle.

15. A medical safety device according to claim 14, wherein the distal end of the first leg is confined within the second leg when the legs are in the first position.

16. A medical safety device according to claim 15, wherein the distal end of the second leg is rounded and tapered.

17. A medical safety device according to claim 14, wherein each of the cam portions includes a substantially tapered profile having a narrow distal end and an enlarged proximal end.

18. A medical safety device, comprising:
a needle hub having a needle supported thereon; and
a safety shield operatively mounted on the needle hub, the safety shield including:
   a pair of spaced legs and a foot member, each of the leas having a distal segment and a proximal segment, each of the proximal segments having a proximal end hingedly attached to the foot member and a distal end hingedly attached to the distal segment at a hinge member, each proximal segment including a camming surface; and
   a trigger supported on the foot member, wherein the trigger includes:
      a camming member and being movable to move the camming member into engagement with the camming surfaces of the proximal segments to effect movement of the legs from a first position in which the distal ends of the distal segments shield a distal end of the needle to a second position in which the distal end of the needle is at least partially exposed; and
      an attachment end configured for selective pivotable attachment to the foot member, wherein the trigger is removable secured to the foot member such that the trigger can be removed from the foot member to prevent movement of the legs from the first position to the second position, and wherein the attachment end of the trigger includes a air of ears each including a pin extending therefrom for pivotable engagement in a complementary feature formed in the foot member.

19. A medical safety device comprising:
a safety shield adapted to be operatively mounted on a needle hub, the safety shield including a pair of spaced legs and a foot member, each of the legs having a distal segment and a proximal segment, each of the proximal segments having a proximal end hingedly attached to the foot member and a distal end hingedly attached to the distal segment at a hinge member, each proximal segment including a camming surface, the safety shield further including a trigger supported on the foot member, the trigger including a camming member and being movable to move the camming member into engagement with the camming surfaces of the proximal segments to effect movement of the legs from a first position in which the distal ends of the distal segments shield a distal end of the needle to a second position in which the distal end of the needle is at least partially exposed, the safety shield further including a piece of spring wire secured to each leg, the piece of spring wire having a proximal end engaging the foot member and a distal end extending along at least a portion of a respective one of the legs, the pieces of spring wire urging the legs to the first position.

* * * * *